(12) United States Patent
Lee et al.

(10) Patent No.: US 11,401,546 B2
(45) Date of Patent: Aug. 2, 2022

(54) DETECTION OF TARGET NUCLEIC ACID SEQUENCES BY PTO CLEAVAGE AND EXTENSION-DEPENDENT EXTENSION ASSAY

(71) Applicant: SEEGENE, INC., Seoul (KR)

(72) Inventors: Young Jo Lee, Seoul (KR); Han Bit Lee, Seoul (KR); Dae Young Kim, Seoul (KR)

(73) Assignee: SEEGENE, INC., Seoul (KR)

( * ) Notice: Subject to any disclaimer, the term of this patent is extended or adjusted under 35 U.S.C. 154(b) by 176 days.

(21) Appl. No.: 16/648,004

(22) PCT Filed: Sep. 27, 2018

(86) PCT No.: PCT/KR2018/011373
§ 371 (c)(1),
(2) Date: Mar. 17, 2020

(87) PCT Pub. No.: WO2019/066461
PCT Pub. Date: Apr. 4, 2019

(65) Prior Publication Data
US 2020/0270679 A1 Aug. 27, 2020

(30) Foreign Application Priority Data
Sep. 29, 2017 (KR) .................. 10-2017-0128110

(51) Int. Cl.
*C12Q 1/68* (2018.01)
*C12Q 1/6851* (2018.01)
*C12Q 1/6853* (2018.01)

(52) U.S. Cl.
CPC ......... *C12Q 1/6851* (2013.01); *C12Q 1/6853* (2013.01); *C12Q 2525/119* (2013.01);
(Continued)

(58) Field of Classification Search
CPC ....................................................... C12Q 1/68
(Continued)

(56) References Cited

U.S. PATENT DOCUMENTS 5,210,015 A 5/1993 Gelfand et al.
5,487,972 A 1/1996 Gelfand et al.
(Continued)

FOREIGN PATENT DOCUMENTS

EP 1548635 A1 6/2005
EP 1564306 A2 8/2005
(Continued)

OTHER PUBLICATIONS

International Search Report from corresponding PCT Application No. PCT/KR2018/011373, dated Apr. 18, 2019.
(Continued)

*Primary Examiner* — Aaron A Priest
(74) *Attorney, Agent, or Firm* — Harness, Dickey & Pierce, P.L.C.

(57) ABSTRACT

The present invention relates to the detection of a target nucleic acid sequence by a PTOCE-E (PTO Cleavage and Extension-dependent Extension) assay. The PTOCE-E assay of the present invention can reduce the non-target signal and increase the target signal as compared with the conventional PTOCE and PCE-SH methods, thereby enabling more accurate detection of the target nucleic acid sequence.

21 Claims, 4 Drawing Sheets

Specification includes a Sequence Listing.

(52) U.S. Cl.
CPC . *C12Q 2525/161* (2013.01); *C12Q 2525/185* (2013.01); *C12Q 2527/107* (2013.01); *C12Q 2561/101* (2013.01)

(58) Field of Classification Search
USPC ........................................................ 435/6.12
See application file for complete search history.

(56) References Cited

U.S. PATENT DOCUMENTS

| | | | |
|---|---|---|---|
| 5,538,848 | A | 7/1996 | Livak et al. |
| 5,631,129 | A * | 5/1997 | Chu .................... C12Q 1/6867 435/5 |
| 5,691,142 | A | 11/1997 | Dahlberg et al. |
| 5,994,069 | A | 11/1999 | Hall et al. |
| 6,326,145 | B1 | 12/2001 | Whitcombe et al. |
| 6,893,819 | B1 | 5/2005 | Sorge |
| 7,381,532 | B2 | 6/2008 | Sorge |
| 7,422,850 | B2 | 9/2008 | Marshall et al. |
| 2002/0045738 | A1 | 4/2002 | Singh et al. |
| 2004/0191823 | A1 | 9/2004 | Virgos et al. |
| 2005/0142595 | A1 | 6/2005 | Maletta et al. |
| 2005/0221315 | A1 | 10/2005 | Braven et al. |
| 2006/0110748 | A1* | 5/2006 | Sorge .................... C12Q 1/6844 435/6.1 |
| 2006/0246469 | A1 | 11/2006 | Sorge |
| 2007/0099211 | A1* | 5/2007 | Aivazachvili ........ C12Q 1/6825 435/5 |
| 2007/0231815 | A1 | 10/2007 | Sorge |
| 2008/0131890 | A1 | 6/2008 | Allawi et al. |
| 2008/0160535 | A1 | 7/2008 | Gold et al. |
| 2008/0187910 | A1 | 8/2008 | Nilsen |
| 2008/0193940 | A1 | 8/2008 | Aivazachvili et al. |
| 2008/0241838 | A1 | 10/2008 | Scaboo et al. |
| 2009/0305237 | A1 | 12/2009 | Cantor et al. |
| 2010/0041049 | A1 | 2/2010 | Smith et al. |
| 2011/0171649 | A1 | 7/2011 | Kutyavin |
| 2011/0281266 | A1 | 11/2011 | Sergeev et al. |
| 2013/0109588 | A1* | 5/2013 | Chun .................... C12Q 1/6837 506/9 |
| 2013/0295688 | A1 | 11/2013 | Bailey et al. |

FOREIGN PATENT DOCUMENTS

| | | |
|---|---|---|
| EP | 2256216 A1 | 12/2010 |
| JP | 2003334097 A | 11/2003 |
| JP | 2004305219 A | 11/2004 |
| KR | 2009-0067334 A | 6/2009 |
| WO | WO-1998023774 A1 | 6/1998 |
| WO | WO-2004084125 A1 | 9/2004 |
| WO | WO-2005010199 A2 | 2/2005 |
| WO | WO-2005059548 A1 | 6/2005 |
| WO | WO-2006004949 A1 | 1/2006 |
| WO | WO-2006005081 A2 | 1/2006 |
| WO | WO-2008076948 A1 | 6/2008 |
| WO | WO-2008094902 A2 | 8/2008 |
| WO | WO-2008102057 A1 | 8/2008 |
| WO | WO-2009117327 A2 | 9/2009 |
| WO | WO-2010055134 A1 | 5/2010 |
| WO | WO-2010128041 A1 | 11/2010 |
| WO | WO-2011028041 A2 | 3/2011 |
| WO | WO-2011078441 A1 | 6/2011 |
| WO | WO-2012096523 A2 | 7/2012 |
| WO | WO-2012134195 A2 | 10/2012 |
| WO | WO-2013115442 A1 | 8/2013 |
| WO | WO-2013133561 A1 | 9/2013 |
| WO | WO-2013-157821 A1 | 10/2013 |
| WO | WO-2013157821 A1 * | 10/2013 ........... C12Q 1/6818 |
| WO | WO-2014-014988 A2 | 1/2014 |
| WO | WO-2014014988 A2 * | 1/2014 ........... C12Q 1/6853 |
| WO | WO-2014073534 A1 | 5/2014 |
| WO | WO-2015-057008 A2 | 4/2015 |
| WO | WO-2015057008 A2 * | 4/2015 ........... C12Q 1/6832 |

OTHER PUBLICATIONS

Allawi, H., et al.; Quantitation of microRNAs using a modified Invader assay; RNA Society, vol. 10,2004, pp. 1153-1161.

Lyamichev, V., et al.; Polymorphism identification and quantitative detection of genomic DNA by invasive cleavage of oligonucleotide probes; 1999 Nature America Inc., Nature Biotechnology, vol. 17. Mar. 1999, pp. 292-296.

Olivier, M.; The Invader(R) assay of SNP genotyping; Elsevier, Mutation Research, vol. 573, 2005, pp. 103-110.

Roux. P. et al.; Direct Measurement of Multiple mRNAs in Nerve Growth Factor-Induced PC12 Cells Using Electrophoretic Tags to Monitor Biomarkers of Neuronal Differentiation in 96-Well Format; ASSAY and Drug Development Technologies, vol. 2, No. 6, 2004, pp. 637-646.

Lohmann et al. A new enzymatic route for production of long 5'-phosphorylated oligonucleotides using Suicide cassettes and rolling circle DNA synthesis. BMC Biotechnology. 2007, vol. 7, No. 49.

Hessner et al. Genotyping of Factor VG1691A (Leiden) without the Use of PCR by Invasive Cleavage of Oligonucleotide Probes. Clinical Chemistry, vol. 46, 2000, No. 8, pp. 1051-1056.

Nurmi, et al. A new label technology for the detection of specific polymerase chain reaction products in a closed tube. Nucleic Acids Research, 28, e280, 2000.

Weiner, M., et al.: Kits and their unique role in molecular biology: a brief retrospective; BioTechniques 44: 701-704, Apr. 2008.

* cited by examiner

A. Probing and Tagging Oligonucleotide (PTO)

B. First Capturing and Templating Oligonucleotide (First CTO)

C. Second Capturing and Templating Oligonucleotide (Second CTO)

A. Hybridization of PTO

B. Cleavage of PTO

C. Formation of First extended duplex

D. Formation of Second extended duplex

Formation of Second extended duplex

```
                         SEQUENCE LISTING

<160> NUMBER OF SEQ ID NOS: 5

<210> SEQ ID NO 1
    <211> LENGTH: 27
    <212> TYPE: DNA
    <213> ORGANISM: Artificial Sequence
    <220> FEATURE:
    <223> OTHER INFORMATION: Synthetic oligonucleotide: FPm

<400> SEQUENCE: 1
atgttctaat atagtcacat tttcatt                                           27

<210> SEQ ID NO 2
    <211> LENGTH: 24
    <212> TYPE: DNA
    <213> ORGANISM: Artificial Sequence
    <220> FEATURE:
    <223> OTHER INFORMATION: Synthetic oligonucleotide: RPm

<400> SEQUENCE: 2
ctctattgtt ggatcatatt cgtc                                              24

<210> SEQ ID NO 3
    <211> LENGTH: 38
    <212> TYPE: DNA
    <213> ORGANISM: Artificial Sequence
    <220> FEATURE:
    <223> OTHER INFORMATION: Synthetic oligonucleotide: PTO

<400> SEQUENCE: 3
gtcgcgcgta atcggtggcg taggcaagag tgccttga                               38

<210> SEQ ID NO 4
    <211> LENGTH: 31
    <212> TYPE: DNA
    <213> ORGANISM: Artificial Sequence
    <220> FEATURE:
    <223> OTHER INFORMATION: Synthetic oligonucleotide: First CTO

<400> SEQUENCE: 4
gtacgcggtc gacggtgcga ttacgcgcga c                                      31

<210> SEQ ID NO 5
    <211> LENGTH: 34
    <212> TYPE: DNA
    <213> ORGANISM: Artificial Sequence
    <220> FEATURE:
    <223> OTHER INFORMATION: Synthetic oligonucleotide: Second CTO

<400> SEQUENCE: 5
ggtggatgac gcgcgttttg tacgcggtcg acgg                                   34
```

DETECTION OF TARGET NUCLEIC ACID SEQUENCES BY PTO CLEAVAGE AND EXTENSION-DEPENDENT EXTENSION ASSAY

CROSS-REFERENCE TO RELATED APPLICATIONS

This application Is a national phase application of PCT Application No. PCT/KR2018/011373 filed on Sep. 27, 2018, which claims priority to Korean Patent Application No. 10-2017-0128110 flied on Sep. 29, 2017. The entire disclosures of the applications identified in this paragraph are incorporated herein by reference.

BACKGROUND OF THE INVENTION

Field of the Invention

The present invention relates to the detection of a target nucleic acid sequence by a PTOCE-E (PTO Cleavage and Extension-dependent Extension) assay.

Description of the Related Art

For detection of target nucleic acid sequences, real-time detection methods are widely used to detect target nucleic acid sequences with monitoring target amplification in a real-time manner. The real-time detection methods generally use labeled probes or primers specifically hybridized with target nucleic acid sequences. The exemplified methods by use of hybridization between labeled probes and target nucleic acid sequences include Molecular beacon method using dual-labeled probes with hairpin structure (Tyagi et al, Nature Biotechnology v. 14 March 1996), HyBeacon method (French D J et al., Mol. Cell Probes, 15(6):363-374 (2001)), Hybridization probe method using two probes labeled each of donor and acceptor (Bernard et al, 147-148 Clin Chem 2000; 46) and Lux method using single-labeled oligonucleotides (U.S. Pat. No. 7,537,886). TaqMan method (U.S. Pat. Nos. 5,210,015 and 5,538,848) using dual-labeled probes and its cleavage by 5'-nuclease activity of DNA polymerase is also widely employed in the art.

The exemplified methods using labeled primers include Sunrise primer method (Nazarenko et al, 2516-2521 Nucleic Acids Research, 1997, v. 25 no. 12, and U.S. Pat. No. 6,117,635), Scorpion primer method (Whitcombe et al, 804-807, Nature Biotechnology v. 17 Aug. 1999 and U.S. Pat. No. 6,326,145) and TSG primer method (WO 2011/078441).

As alternative approaches, real-time detection methods using duplexes formed depending on the presence of target nucleic acid sequences have been proposed: Invader assay (U.S. Pat. Nos. 5,691,142, 6,358,691 and 6,194,149), PTOCE (PTO Cleavage and Extension) method (WO 2012/096523), PCE-SH (PTO Cleavage and Extension-Dependent Signaling Oligonucleotide Hybridization) method (WO 2013/115442), PCE-SC (PTO Cleavage and Extension-dependent Signaling Oligonucleotide Cleavage) (WO 2013/157821), PCE-NH (PTO Cleavage and Extension-Dependent Non-Hybridization) method (WO 2014/104818), PCE-IH (PTO Cleavage and Extension-dependent Immobilized Oligonucleotide Hybridization) (WO 2015/008985).

However, these methods have several drawbacks such as decreased target signals or increased non-target signals, in particular in a multiplex amplification reaction.

Therefore, there remain long-felt needs in the art to develop novel approaches that can reduce non-target signals in detection of nucleotide variation while maintaining target signals.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel approaches to detect target sequences with more improved accuracy and convenience, inter alia, in a multiplex manner. As a result, we have established novel protocols for detection of target sequences, in which target detection is accomplished by probe hybridization as well as by a primary enzymatic reaction of cleavage and extension, and a secondary enzymatic reaction of further extension. The present protocols are well adopted to liquid phase reactions as well as solid phase reactions, and ensure detection of multiple target sequences with more improved accuracy and convenience.

Therefore, it is an object of this invention to provide a method for detecting a target nucleic acid sequence from a DNA or a mixture of nucleic acids by a PTOCE-E (PTO Cleavage and Extension-dependent Extension) assay.

It is another object of this invention to provide a kit for use in the method as described above.

Other objects and advantages of the present invention will become apparent from the detailed description to follow taken in conjugation with the appended claims and drawings.

DETAILED DESCRIPTION OF THIS INVENTION

Figure 1:
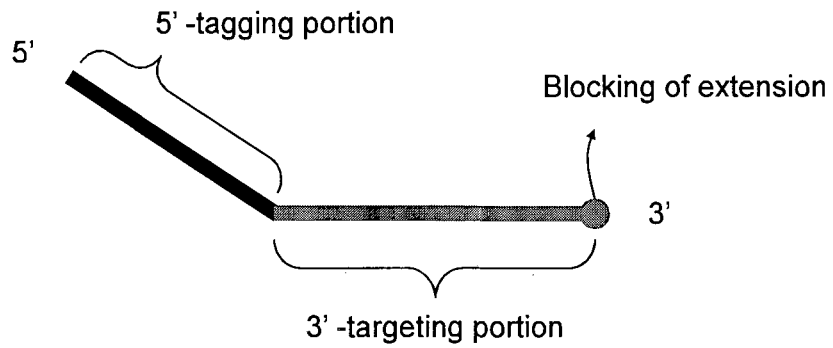
FIG. 1 shows the schematic structures of oligonucleotides used in a "PTO Cleavage and Extension-dependent Extension" (referred herein to as "PTOCE-E") assay of the present invention. A: Probing and Tagging Oligonucleotide (PTO); B: First Capturing and Templating Oligonucleotide (First CTO); C: Second Capturing and Templating Oligonucleotide (Second CTO). As one example, the second CTO is labeled with an interactive dual label comprising a reporter molecule (R) and a quencher molecule (Q) at its templating portion.
Figure 1:
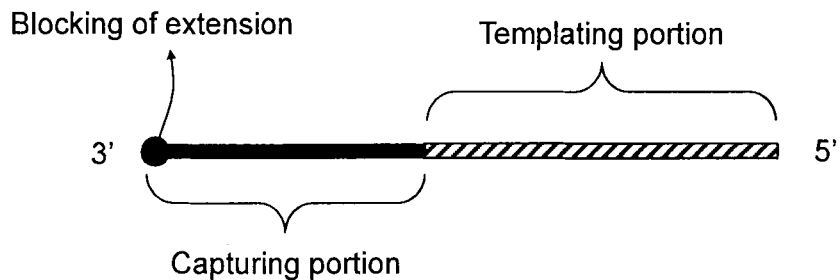
Figure 1:
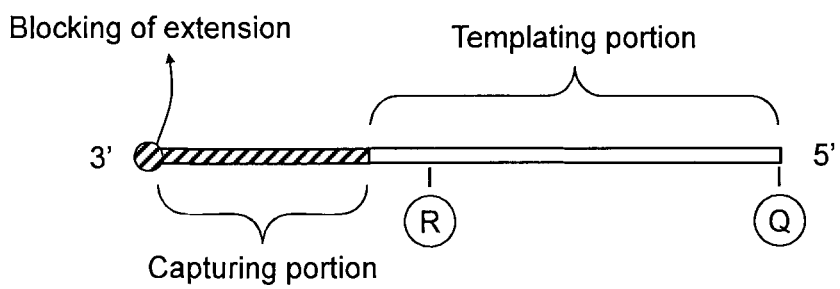

I. Detection of Target Nucleic Acid Sequence by PTOCE-E Assay

In one aspect of the present invention, there is provided a method for detecting a target nucleic acid sequence from a DNA or a mixture of nucleic acids by a PTOCE-E (PTO Cleavage and Extension-dependent Extension) assay, comprising:

(a) hybridizing the target nucleic acid sequence with an upstream oligonucleotide and a PTO (Probing and Tagging Oligonucleotide); wherein the upstream oligonucleotide comprises a hybridizing nucleotide sequence to the target nucleic acid sequence; wherein the PTO comprises (i) a 3'-targeting portion comprising a hybridizing nucleotide sequence to the target nucleic acid sequence and (ii) a 5'-tagging portion comprising a non-hybridizing nucleotide sequence to the target nucleic acid sequence; wherein the 3'-targeting portion of the PTO is hybridized with the target nucleic acid sequence and the 5'-tagging portion of the PTO is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity to release a PTO fragment comprising the 5'-tagging portion or a part of the 5'-tagging portion of the PTO;

(c) hybridizing the PTO fragment with a first CTO (Capturing and Templating Oligonucleotide); wherein the first CTO comprises in a 3' to 5' direction (i) a capturing portion comprising a hybridizing nucleotide sequence to the PTO fragment and (ii) a templating portion comprising a non-hybridizing nucleotide sequence to the PTO fragment; wherein the PTO fragment is hybridized with the capturing portion of the first CTO;

(d) performing an extension reaction using the resultant of the step (c) and a template-dependent nucleic add polymerase; wherein the PTO fragment hybridized with the capturing portion of the first CTO is extended to generate a first extended strand comprising a first extended sequence complementary to the templating portion of the first CTO, thereby forming a first extended duplex between the first extended strand and the first CTO;

(e) hybridizing the first extended strand with a second CTO; wherein the second CTO comprises in a 3' to 5' direction (i) a capturing portion comprising a hybridizing nucleotide sequence to the first extended strand and (ii) a templating portion comprising a non-hybridizing nucleotide sequence to the first extended strand; wherein the first extended strand is hybridized with the capturing portion of the second CTO;

(f) performing an extension reaction using the resultant of the step (e) and a template-dependent nucleic acid polymerase; wherein the first extended strand hybridized with the capturing portion of the second CTO is further extended to generate a second extended strand comprising a second extended sequence complementary to the templating portion of the second CTO, thereby forming a second extended duplex between the second extended strand and the second CTO; and (g) detecting the presence of the second extended strand; whereby the presence of the second extended strand indicates the presence of the target nucleic acid sequence.

The present inventors have made intensive researches to develop novel approaches to detect target sequences with more improved accuracy and convenience, inter alia, in a multiplex manner. As a result, we have established novel protocols for detection of target sequences, in which target detection is accomplished by probe hybridization as well as by a primary enzymatic reaction of cleavage and extension, and a secondary enzymatic reaction of further extension. The present protocols are well adopted to liquid phase reactions as well as solid phase reactions, and ensure detection of multiple target sequences with more improved accuracy and convenience.

The method of the present invention employs successive events occurred by probe hybridization, i.e., cleavage, extension and additional extension of PTO, which is termed "PTO Cleavage and Extension-dependent Extension (PTOCE-E)" assay.

Oligonucleotides used in the PTOCE-E assay of the present invention include an upstream oligonucleotide (and optionally a downstream oligonucleotide); a PTO; a first CTO; and a second CTO. The oligonucleotides are involved in hybridization with a target nucleic acid sequence or reaction products. Unless otherwise stated herein, it should be understood that each oligonucleotide is not hybridized with a target nucleic acid sequence or with other oligonucleotides.

Figure 2:
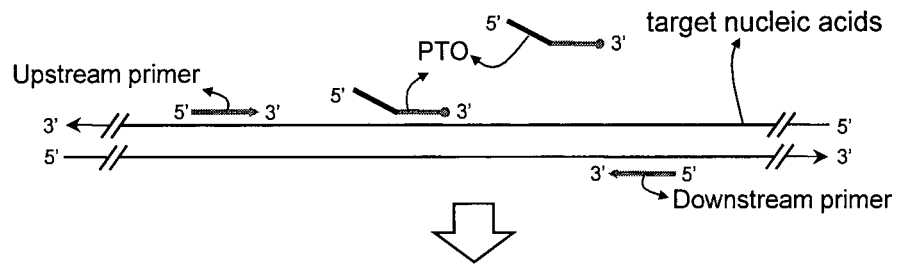
FIG. 2 represents schematically a PTOCE-E assay in accordance with the present invention. An upstream primer, the PTO, and a downstream primer are hybridized with a target nucleic acid sequence (A: hybridization of PTO). The PTO is cleaved by an enzyme having a 5' nuclease activity through the extension of the upstream primer, releasing a PTO fragment (B: cleavage of PTO). The PTO fragment is hybridized with the first CTO and extended to form a first extended duplex between the first extended strand the first CTO; whereas an uncleaved PTO is hybridized with the first CTO, but not extended (C: formation of First extended duplex). The first extended strand is hybridized with the second CTO and further extended to form a second extended duplex between the second extended strand and the second CTO, and the second extended duplex produces a signal indicative of the presence of the target nucleic acid sequence (D: Formation of Second extended duplex).
Figure 2:
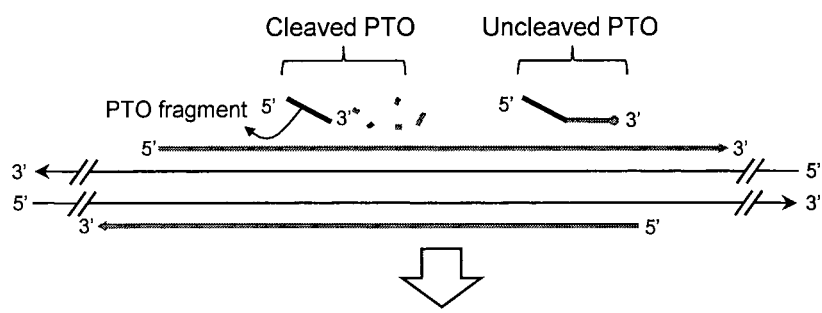
Figure 2:
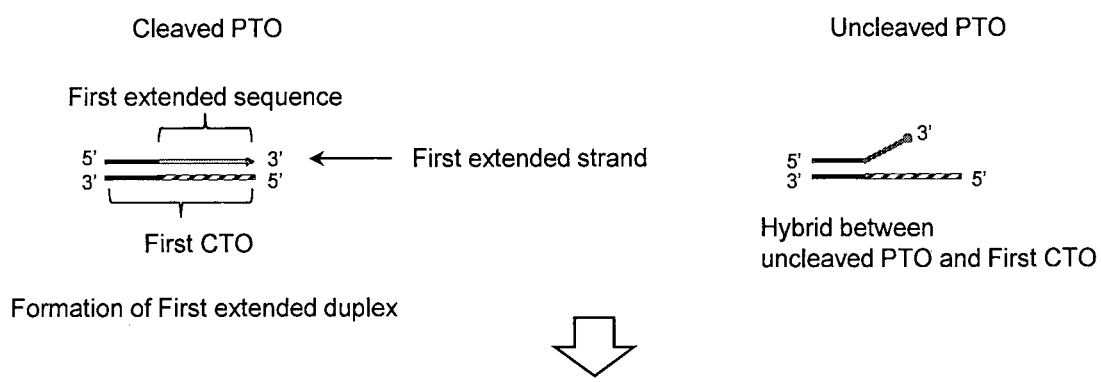
Figure 2:
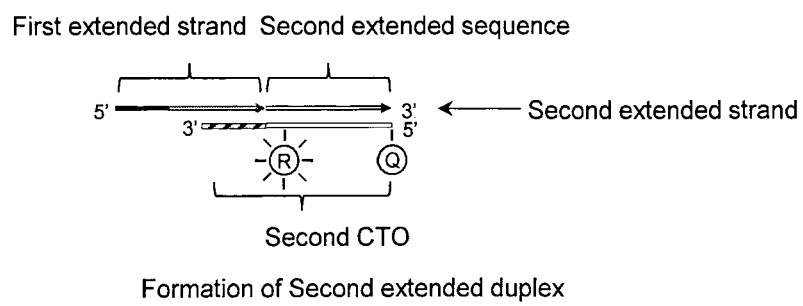

The PTOCE-E assay of the present invention is schematically illustrated in FIG. 2. The PTOCE-E assay will be described in more detail as follows:

Step (a): Hybridization of Upstream Oligonucleotide and PTO with Target Nucleic Acid Sequence According to the present invention, a target nucleic acid sequence is hybridized with an upstream oligonucleotide and a PTO (Probing and Tagging Oligonucleotide).

The term "target nucleic acid", "target nucleic acid sequence" or "target sequence" as used herein refers to a nucleic acid sequence of interest for detection, which is annealed to or hybridized with a probe or primer under hybridization, annealing or amplifying conditions.

The term "probe" as used herein refers to a single-stranded nucleic acid molecule comprising a hybridizing portion(s) to a target nucleic acid sequence.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

Particularly, the probe and primer are single-stranded deoxyribonucleotide molecules. The probes or primers used in this invention may be comprised of naturally occurring dNMP (i.e., dAMP, dGM, dCMP and dTMP), modified nucleotide, or non-natural nucleotide. The probes or primers may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term "hybridize", "hybridizing" or "hybridization" as used herein refers to the formation of double strands by noncovalent association between two complementary single-stranded polynucleotides under certain hybridization conditions or stringent conditions.

In particular, the expression herein that one oligonucleotide "comprises a hybridizing nucleotide sequence" to another oligonucleotide refers to all or a portion of one oligonucleotide has a complementary nucleotide sequence necessary for hybridization with all or a portion of another oligonucleotide.

Further, when referring to hybridization of a portion of one oligonucleotide to another oligonucleotide, the portion of one oligonucleotide can be regarded as an individual oligonucleotide.

The hybridization may occur between two nucleic acid strands perfectly matched or substantially matched with some mismatches (e.g., 1-4 mismatches). The complementarity for hybridization may depend on hybridization conditions, particularly temperature.

The hybridization of a target nucleic acid sequence with the upstream oligonucleotide and the PTO may be carried out under suitable hybridization conditions routinely determined by optimization procedures. Conditions such as temperature, concentration of components, hybridization and washing times, buffer components, and their pH and ionic strength may be varied depending on various factors, including the length and GC content of oligonucleotide (upstream oligonucleotide and PTO) and the target nucleotide sequence. For instance, when a relatively short oligonucleotide is used, it is preferable that low stringent conditions are adopted. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999).

There is no intended distinction between the terms "annealing" and "hybridizing", and these terms will be used interchangeably.

The upstream oligonucleotide and PTO have hybridizing nucleotide sequences complementary to the target nucleic acid sequence. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", particularly perfectly complementary.

In contrast, the term "non-complementary" is used herein mean that primers or probes are sufficiently non-complementary not to hybridize selectively to a target nucleic acid sequence under the designated annealing conditions or stringent conditions, encompassing the terms "substantially non-complementary" and "perfectly non-complementary", particularly perfectly non-complementary.

As used herein, the term "PTO (Probing and Tagging Oligonucleotide)" means an oligonucleotide comprising (i) a 3'-targeting portion comprising a hybridizing nucleotide sequence to the target nucleic acid sequence and (ii) a 5'-tagging portion comprising a non-hybridizing nucleotide sequence to the target nucleic acid sequence; wherein the 3'-targeting portion of the PTO is hybridized with the target nucleic acid sequence and the 5'-tagging portion of the PTO is not hybridized with the target nucleic acid sequence.

The PTO is schematically illustrated in FIG. 1. As illustrated in FIG. 1, the PTO comprises two portions as follows: (i) a 3'-targeting portion serving as a probe and (ii) a 5'-tagging portion with a non-hybridizing nucleotide sequence to the target nucleic acid sequence, which is nucleolytically released from the PTO after hybridization with the target nucleic acid sequence. The 5'-tagging portion and the 3'-targeting portion in the PTO have to be positioned in a 5' to 3' order.

Particularly, the hybridization in step (a) is performed under stringent conditions that the 3'-targeting portion is hybridized with the target nucleic acid sequence and the 5'-tagging portion is not hybridized with the target nucleic acid sequence.

The PTO does not require any specific lengths. For example, the length of the PTO may be 15-150 nucleotides, 15-100 nucleotides, 15-80 nucleotides, 15-60 nucleotides, 15-40 nucleotides, 20-150 nucleotides, 20-100 nucleotides, 20-80 nucleotides, 20-60 nucleotides, 20-50 nucleotides, 30-150 nucleotides, 30-100 nucleotides, 30-80 nucleotides, 30-60 nucleotides, 30-50 nucleotides, 35-100 nucleotides, 35-80 nucleotides, 35-60 nucleotides, or 35-50 nucleotides.

The 3'-targeting portion of the PTO may be in any lengths so long as it is specifically hybridized with target nucleic acid sequences. For example, the 3'-targeting portion of the PTO may be 10-100 nucleotides, 10-80 nucleotides, 10-50 nucleotides, 10-40 nucleotides, 10-30 nucleotides, 15-100 nucleotides, 15-80 nucleotides, 15-50 nucleotides, 15-40 nucleotides, 15-30 nucleotides, 20-100 nucleotides, 20-80 nucleotides, 20-50 nucleotides, 20-40 nucleotides or 20-30 nucleotides in length.

The 5'-tagging portion may be in any lengths so long as it is specifically hybridized with the templating portion of the first CTO and then extended. For instance, the 5'-tagging portion of the PTO may be 5-50 nucleotides, 5-40 nucleotides, 5-30 nucleotides, 5-20 nucleotides, 10-50 nucleotides, 10-40 nucleotides, 10-30 nucleotides, 10-20 nucleotides, 15-50 nucleotides, 15-40 nucleotides, 15-30 nucleotides or 15-20 nucleotides in length.

The 3'-end of the PTO may have a 3'-OH terminal. Particularly, the 3'-end of the PTO is "blocked" to prohibit its extension.

The blocking may be achieved in accordance with conventional methods. For instance, the blocking may be performed by adding to the 3'-hydroxyl group of the last nucleotide a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

Alternatively, the PTO may be designed to have a hairpin structure.

The non-hybridization between the 5'-tagging portion of the PTO and the target nucleic acid sequence refers to non-formation of a stable double-strand between them under certain hybridization conditions. According to an embodiment, the 5'-tagging portion of the PTO not involved in the hybridization with the target nucleic acid sequence forms a single-strand.

The "upstream oligonucleotide" used in the present method refers to an oligonucleotide located upstream of the PTO. When a target nucleic acid sequence is double stranded, the upstream oligonucleotide and the PTO are hybridized with one strand of the double stranded target nucleic acid, and the PTO is positioned downstream of the upstream oligonucleotide. The upstream oligonucleotide is hybridized with a specific portion in the 3'-direction relative to the portion of the target nucleic acid strand to which the PTO is hybridized.

The upstream oligonucleotide or its extended strand hybridized with the target nucleic acid sequence induces cleavage of the PTO by an enzyme having a 5' nuclease activity.

The induction of the PTO cleavage by the upstream oligonucleotide may be accomplished by two fashions: (i) upstream oligonucleotide extension-independent cleavage induction; and (ii) upstream oligonucleotide extension-dependent cleavage induction.

Where the upstream oligonucleotide is positioned adjacently to the PTO sufficient to induce the PTO cleavage by an enzyme having a 5' nuclease activity, the enzyme bound to the upstream oligonucleotide digests the PTO with no extension reaction. In contrast, where the upstream oligonucleotide is positioned distantly to the PTO, an enzyme having a polymerase activity (e.g., template-dependent polymerase) catalyzes extension of the upstream oligonucleotide (e.g., upstream primer) and an enzyme having a 5' nuclease activity bound to the extended product digests the PTO.

Therefore, the upstream oligonucleotide may be located relatively to the PTO in two fashions. The upstream oligonucleotide may be located adjacently to the PTO sufficient to induce the PTO cleavage in an extension-independent manner. Alternatively, the upstream oligonucleotide may be located distantly to the PTO sufficient to induce the PTO cleavage in an extension-dependent manner.

The term used herein "adjacent" with referring to positions or locations means that the upstream oligonucleotide is located adjacently to the 3'-targeting portion of the PTO to form a nick. Also, the term means that the upstream oligonucleotide is located 1-30 nucleotides, 1-20 nucleotides or 1-15 nucleotides apart from the 3'-targeting portion of the PTO.

The term used herein "distant" with referring to positions or locations includes any positions or locations sufficient to ensure extension reactions.

According to a particular embodiment, the upstream oligonucleotide is located distantly to the PTO sufficient to induce the PTO cleavage in an extension-dependent manner.

According to a particular embodiment, the upstream oligonucleotide is an upstream primer or an upstream probe. The upstream primer is suitable in an extension-independent cleavage induction or an extension-dependent cleavage, and the upstream probe is suitable in an extension-independent cleavage induction.

Alternatively, the upstream oligonucleotide may have a partial-overlapped sequence with the 5'-part of the 3'-targeting portion of the PTO. Particularly, the overlapped sequence is 1-10 nucleotides, more particularly 1-5 nucleotides, still more particularly 1-3 nucleotides in length. Where the upstream oligonucleotide has a partial-overlapped sequence with the 5'-part of the 3'-targeting portion of the PTO, the 3'-targeting portion is partially digested along with the 5'-tagging portion in the cleavage reaction of the step (b). In addition, the overlapped sequence permits to cleave a desired site of the 3'-targeting portion.

According to a particular embodiment, the upstream primer induces through its extended strand the cleavage of the PTO by the enzyme having the 5' nuclease activity.

The conventional technologies for cleavage reactions by upstream oligonucleotides may be applied to the present invention, so long as the upstream oligonucleotide induces cleavage of the PTO hybridized with the target nucleic acid sequence to release a fragment comprising the 5'-tagging portion or a part of the 5'-tagging portion of the PTO. For example, U.S. Pat. Nos. 5,210,015, 5,487,972, 5,691,142, 5,994,069 and 7,381,532 and U.S. Appln. Pub. No. 2008-0241838 may be applied to the present invention.

According to a particular embodiment, the method is performed in the presence of a downstream primer. The downstream primer may also be referred to as a reverse primer. The downstream primer is hybridized to a nucleic acid strand complementary to a nucleic acid strand to which an upstream primer and the PTO are hybridized. In particular, the downstream primer hybridizes to a specific portion in the 3'-direction relative to a portion of a nucleic acid strand complementary to a portion of a nucleic acid strand to which the PTO is hybridized. The downstream primer generates additionally a target nucleic acid sequence to be hybridized with the PTO, enhancing sensitivity in target detection.

According to an embodiment, when the upstream primer and the downstream primer are used, a template-dependent nucleic acid polymerase is additionally employed for extension of the primers.

According to a preferred embodiment, the upstream oligonucleotide (upstream primer or upstream probe), the downstream primer and/or 5'-tagging portion of the PTO have a dual priming oligonucleotide (DPO) structure developed by the present inventor. The oligonucleotides having the DPO structure show significantly improved target specificity compared with conventional primers and probes (see WO 2006/095981; Chun et al., Dual priming oligonucleotide system for the multiplex detection of respiratory viruses and SNP genotyping of CYP2C19 gene, *Nucleic Acid Research*, 35: 6e40(2007)).

According to an embodiment, the 3'-targeting portion of the PTO has a modified dual specificity oligonucleotide (mDSO) structure developed by the present inventor. The modified dual specificity oligonucleotide (mDSO) structure shows significantly improved target specificity compared with conventional probes (see WO 2011/028041)

Step (b): Cleavage of PTO

Afterwards, the resultant of the step (a) is contacted to an enzyme having a 5' nuclease activity under conditions for cleavage of the PTO. The upstream oligonucleotide or its extended strand induces cleavage of the PTO by the enzyme having the 5' nuclease activity to releases a PTO fragment comprising the 5'-tagging portion or a part of the 5'-tagging portion of the PTO.

The phrase "conditions for cleavage of the PTO" as used herein means conditions sufficient to digest the PTO hybridized with the target nucleic acid sequence by the enzyme having the 5' nuclease activity, such as temperature, pH, ionic strength, buffer, length and sequence of oligonucleotides and enzymes. For example, when Taq DNA polymerase is used as the enzyme having the 5' nuclease activity, the conditions for cleavage of the PTO include Tris-HCl buffer, KCl, $MgCl_2$ and temperature.

When the PTO is hybridized with the target nucleic acid sequence, its 3'-targeting portion is involved in the hybridization and its 5'-tagging portion forms a single-strand with no hybridization with the target nucleic acid sequence (see FIG. 2). As such, an oligonucleotide comprising both single-stranded and double-stranded structures may be digested using an enzyme having a 5' nuclease activity by a variety of technologies known to one of skill in the art.

The cleavage sites of the PTO are varied depending on the type of upstream oligonucleotides (upstream probe or upstream primer), hybridization sites of upstream oligonucleotides and cleavage conditions (see U.S. Pat. Nos. 5,210,015, 5,487,972, 5,691,142, 5,994,069 and 7,381,532 and U.S. Appln. Pub. No. 2008-0241838).

A multitude of conventional technologies may be employed for the cleavage reaction of the PTO, releasing a fragment comprising the 5'-tagging portion or a part of the 5'-tagging portion.

Briefly, there may be three sites of cleavage in the step (b). Firstly, the cleavage site is a junction site between a hybridization portion of the PTO (3'-targeting portion) and a non-hybridization portion (5'-tagging portion). The second cleavage site is a site located several nucleotides in a 3'-direction apart from the 3'-end of the 5'-tagging portion of the PTO. The second cleavage site is located at the 5'-end part of the 3'-targeting portion of the PTO. The third cleavage site is a site located several nucleotides in a 5'-direction apart from the 3'-end of the 5'-tagging to portion of the PTO.

According to an embodiment, the initial site for the cleavage of the PTO by the template-dependent polymerase having the 5' nuclease activity upon extension of the upstream primer is a starting point of the double strand between the PTO and the target nucleic acid sequence or a site 1-3 nucleotides apart from the starting point.

In this regard, the phrase "a PTO fragment comprising the 5'-tagging portion or a part of the 5'-tagging portion of the PTO" in the context of cleavage of the PTO by the enzyme having the 5' nuclease activity as used herein is used to encompass (i) the 5'-tagging portion, (ii) the 5'-tagging portion and the 5'-end part of the 3'-targeting portion and (iii) a part of the 5'-tagging portion. The phrase "a fragment comprising the 5'-tagging portion or a part of the 5'-tagging portion of the PTO" may be abbreviated as "PTO fragment".

The term "part" used in conjunction with the PTO or the first or second CTO such as the part of the 5'-tagging portion of the PTO, the 5'-end part of the 3'-targeting portion of the PTO and the 5'-end part of the capturing portion of the first or second CTO refers to a nucleotide sequence composed of 1-40, 1-30, 1-20, 1-15, 1-10 or 1-5 nucleotides, particularly 1, 2, 3 or 4 nucleotides.

According to an embodiment, the enzyme having the 5' nuclease activity is DNA polymerase having a 5' nuclease activity or FEN nuclease, more particularly a thermostable DNA polymerase having a 5' nuclease activity or FEN nuclease.

A suitable DNA polymerase having a 5' nuclease activity in this invention is a thermostable DNA polymerase obtained from a variety of bacterial species, including *Thermus aquaticus* (Taq), *Thermus thermophilus* (Tth), *Thermus filiformis*, *Thermis flavus*, *Thermococcus literalis*, *Thermus antranikianii*, *Thermus caldophilus*, *Thermus chliarophilus*, *Thermus flavus*, *Thermus igniterrae*, *Thermus lacteus*, *Thermus oshimai*; *Thermus ruber*; *Thermus rubens*, *Thermus scotoductus*, *Thermus silvans*, *Thermus* species Z05, *Thermus* species sps 17, *Thermus thermophilus*, *Thermotoga maritima*, *Thermotoga neapolitana*, *Thermosipho africanus*, *Thermococcus litoralis*, *Thermococcus barossi*, *Thermococcus gorgonarius*, *Thermotoga maritima*, *Thermotoga neapolitana*, *Thermosipho africanus*, *Pyrococcus woesei*, *Pyrococcus horikoshii*, *Pyrococcus abyssi*, *Pyrodictium occultum*, *Aquifex pyrophilus* and *Aquifex aeolieus*. Most particularly, the thermostable DNA polymerase is Taq polymerase.

Alternatively, the present invention may employ DNA polymerases having a 5' nuclease activity modified to have less polymerase activities.

The FEN (flap endonuclease) nuclease used is a 5' flap-specific nuclease.

The FEN nuclease suitable in the present invention comprises FEN nucleases obtained from a variety of bacterial species, including *Sulfolobus solfataricus*, *Pyrobaculum aerophilum*, *Thermococcus litoralis*, *Archaeaglobus veneficus*, *Archaeaglobus profundus*, *Acidianus brierlyi*; *Acidianus ambivalens*, *Desulfurococcus amylolyticus*, *Desulfurococcus mobillis*, *Pyrodictium brockii*, *Thermococcus gorgonarius*, *Thermococcus zilligii*, *Methanopyrus kandleri*; *Methanococcus igneus*, *Pyrococcus horikoshii*, *Aeropyrum pernix*, and *Archaeaglobus veneficus*.

Where the upstream primer is used in the step (a), it is preferable that the conditions for cleavage of the PTO comprise extension reaction of the upstream primer.

According to an embodiment, the upstream primer is used in the step (a), a template-dependent polymerase is used for extension of the upstream primer, and the template-dependent polymerase is identical to the enzyme having the 5' nuclease activity.

According to another embodiment, the upstream primer is used in the step (a), a template-dependent polymerase is used for extension of the upstream primer, and the template-dependent polymerase is different from the enzyme having the 5' nuclease activity.

Step (c): Hybridization of PTO Fragment with First CTO

The fragment released from the PTO is hybridized with a first Capturing and Templating Oligonucleotide (first CTO).

The first CTO comprises in a 3' to 5' direction (i) a capturing portion comprising a hybridizing nucleotide sequence to the PTO fragment and (ii) a templating portion comprising a non-hybridizing nucleotide sequence to PTO fragment; wherein the PTO fragment is hybridized with the capturing portion of the first CTO (see FIG. 2).

The first CTO is acted as a template for extension of the PTO fragment. The PTO fragment as a primer is hybridized with the first CTO and extended to form a first extended duplex.

The templating portion of the first CTO may comprise any sequence so long as it is non-complementary to the 5'-tagging portion and the 3'-targeting portion of the PTO. Furthermore, the templating portion of the first CTO may comprise any sequence so long as it can be acted as a template for extension of the fragment released from the PTO.

The capturing portion of the first CTO comprises a hybridizing nucleotide sequence to the PTO fragment. Alternatively, the capturing portion of the first CTO comprises a hybridizing nucleotide sequence to the 5'-tagging portion of the PTO.

As described above, when the PTO fragment having the 5'-tagging portion of the PTO is released, it is preferred that the capturing portion of the first CTO is designed to comprise a hybridizing or complementary nucleotide sequence to the 5'-tagging portion. When the PTO fragment having the 5'-tagging portion and a 5'-end part of the 3'-targeting portion is released, it is preferred that the capturing portion of the first CTO is designed to comprise a hybridizing or complementary nucleotide sequence to the 5'-tagging portion and the 5'-end part of the 3'-targeting portion. When the PTO fragment having a part of the 5'-tagging portion of the PTO is released, it is preferred that the capturing portion of the first CTO is designed to comprise a hybridizing or complementary nucleotide sequence to the part of the 5'-tagging portion.

Moreover, it is possible to design the capturing portion of the first CTO with anticipating cleavage sites of the PTO. For example, where the capturing portion of the first CTO is designed to comprise a hybridizing or complementary nucleotide sequence to the 5'-tagging portion, either the PTO fragment having a part of the 5'-tagging portion or the PTO fragment having the 5'-tagging portion can be hybridized with the capturing portion of the first CTO and then extended. Where the PTO fragment comprising the 5'-tagging portion and a 5'-end part of the 3'-targeting portion is released, it may be hybridized with the capturing portion of the first CTO designed to comprise a hybridizing or complementary nucleotide sequence to the 5'-tagging portion and then successfully extended although mismatch nucleotides are present at the 3'-end portion of the fragment. That is because primers can be extended depending on reaction conditions although its 3'-end contains some mismatch nucleotides (e.g. 1-4 mismatch nucleotides).

When the PTO fragment comprising the 5'-tagging portion and a 5'-end part of the 3'-targeting portion is released, the 5'-end part of the capturing portion of the first CTO may be designed to have a nucleotide sequence complementary to the cleaved 5'-end part of the 3'-targeting portion, overcoming problems associated with mismatch nucleotides (see FIG. 1).

Particularly, the nucleotide sequence of the 5'-end part of the capturing portion of the first CTO complementary to the cleaved 5'-end part of the 3'-targeting portion may be selected depending on anticipated cleavage sites on the 3'-targeting portion of the PTO. The nucleotide sequence of the 5'-end part of the capturing portion of the first CTO complementary to the cleaved 5'-end part of the 3'-targeting portion is 1-10 nucleotides, 1-5 nucleotides, or 1-3 nucleotides.

The 3'-end of the first CTO may comprise additional nucleotides not involved in hybridization with the PTO fragment. Moreover, the capturing portion of the first CTO may comprise a hybridizing or complementary nucleotide sequence only to a part of the PTO fragment (e.g., a part of the PTO fragment containing its 3'-end portion) so long as it is stably hybridized with the PTO fragment.

The term used "capturing portion comprising a nucleotide sequence complementary to the 5'-tagging portion or a part of the 5'-tagging portion" is described herein to encompass various designs and compositions of the capturing portion of the first CTO as discussed above.

The first CTO may be designed to have a hairpin structure or no hairpin structure.

The length of the first CTO may be widely varied. For example, the first CTO is 5-1000 nucleotides, 5-500 nucleotides, 5-300 nucleotides, 5-100 nucleotides, 5-80 nucleotides, 5-60 nucleotides, 5-40 nucleotides, 7-1000 nucleotides, 7-500 nucleotides, 7-300 nucleotides, 7-100 nucleotides, 7-80 nucleotides, 7-60 nucleotides, 7-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length.

The capturing portion of the first CTO may have any length so long as it is specifically hybridized with the PTO fragment. For example, the capturing portion of the first CTO is 5-100 nucleotides, 5-60 nucleotides, 5-40 nucleotides, 5-30 nucleotides, 5-20 nucleotides, 10-100 nucleotides, 10-60 nucleotides, 10-40 nucleotides, 10-30 nucleotides, 10-20 nucleotides, 15-100 nucleotides, 15-60 nucleotides, 15-40 nucleotides, 15-30 nucleotides or 15-20 nucleotides in length.

The templating portion of the first CTO may have any length so long as it can act as a template in extension of the PTO fragment. For example, the templating portion of the first CTO is 1-900 nucleotides, 1-400 nucleotides, 1-300 nucleotides, 1-100 nucleotides, 1-80 nucleotides, 1-60 nucleotides, 1-40 nucleotides, 1-20 nucleotides, 2-900 nucleotides, 2-400 nucleotides, 2-300 nucleotides, 2-100 nucleotides, 2-80 nucleotides, 2-60 nucleotides, 2-40 nucleotides, 2-20 nucleotides, 5-900 nucleotides, 5-400 nucleotides, 5-300 nucleotides, 5-100 nucleotides, 5-80 nucleotides, 5-60 nucleotides, 5-40 nucleotides, 5-30 nucleotides, 5-60 nucleotides, 5-40 nucleotides, 5-30 nucleotides, 10-900 nucleotides, 10-400 nucleotides, 10-300 nucleotides, 15-900 nucleotides, 15-100 nucleotides, 15-80 nucleotides, 15-60 nucleotides, 15-40 nucleotides or 15-20 nucleotides in length.

The 3'-end of the first CTO may have a 3'-OH terminal. Alternatively, the 3'-end of the first CTO is blocked to prohibit its extension. The non-extendible blocking of the first CTO may be achieved in accordance with conventional methods. For instance, the blocking may be performed by adding to the 3'-hydroxyl group of the last nucleotide of the first CTO a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

The PTO fragment is hybridized with the first CTO, providing a form suitable in extension of the PTO fragment. Although an undigested PTO is also hybridized with the capturing portion of the first CTO through its 5'-tagging portion, its 3'-targeting portion is not hybridized to the first CTO which prohibits the formation of a first extended duplex.

The hybridization in the step (c) can be described in detail with referring to descriptions in the step (a).

Step (d): Extension of PTO Fragment and Formation of First Extended Duplex

The extension reaction is carried out using the resultant of the step (c) and a template-dependent nucleic acid polymerase. The PTO fragment hybridized with the capturing portion of the first CTO is extended to generate a first extended strand comprising a first extended sequence complementary to the templating portion of the first CTO. This results in a first extended duplex between the first extended strand and the first CTO. In contrast, uncleaved PTO hybridized with the capturing portion of the first CTO is not extended such that no first extended duplex is formed.

In the step (d), the PTO fragment hybridized with the capturing portion of the first CTO is extended along the templating portion of the first CTO as a template by a template-dependent nucleic acid polymerase.

The terms "first extended sequence", "first extended strand" and "first extended duplex" as used in connection with the extension reaction of the PTO fragment in step (d) have the following meanings:

As used herein, the term "first extended sequence" refers to a sequence which is newly formed by extension from the PTO fragment in the step (d). In other words, the first extended sequence refers to a portion of the first extended strand as will be described below, excluding the PTO fragment.

As used herein, the term "first extended strand" refers to a sequence encompassing the PTO fragment and the first extended sequence. In other words, the first extended strand refers to a portion of the first extended duplex as will be described below, excluding the first CTO.

As used herein, the term "first extended duplex" refers to a hybrid or duplex (through complementarity) between the first extended strand and the first CTO. In other words, the first extended duplex means a duplex between the first extended strand, composed of the PTO fragment and the first extended sequence, and the first CTO.

It is to be understood that the terms "first extended sequence", "first extended strand" and "first extended duplex" are distinguishable from the terms "second extended sequence", "second extended strand" and "second extended duplex" as described elsewhere herein.

The first extended duplex has different $T_m$ value from the second extended duplex as will be described below.

The $T_m$ value of the first extended duplex is adjustable by (i) a sequence and/or length of the PTO fragment, (ii) a sequence and/or length of the first CTO or (iii) the sequence and/or length of the PTO fragment and the sequence and/or length of the first CTO.

The term used herein "$T_m$" refers to a melting temperature at which half a population of double stranded nucleic acid molecules are dissociated to single-stranded molecules. The $T_m$ value is determined by length and G/C content of nucleotides hybridized. The $T_m$ value may be calculated by conventional methods such as Wallace rule (R. B. Wallace, et al., *Nucleic Acids Research*, 6:3543-3547(1979)) and nearest-neighbor method (SantaLucia J. Jr., et al., *Biochemistry*, 35:3555-3562(1996)); Sugimoto N., et al., *Nucleic Acids Res.*, 24:4501-4505(1996)).

According to a preferred embodiment, the $T_m$ value refers to actual $T_m$ values under reaction conditions actually practiced.

The template-dependent nucleic acid polymerase used in the step (d) may include any nucleic acid polymerases, for example, Klenow fragment of *E. coli* DNA polymerase I, a thermostable DNA polymerase and bacteriophage T7 DNA polymerase. Particularly, the polymerase is a thermostable DNA polymerase which may be obtained from a variety of bacterial species, including *Thermus aquaticus* (Taq), *Thermus thermophilus* (Tth), *Thermus filiformis, Thermis flavus, Thermococcus literalis, Thermus antranikianii, Thermus caldophilus, Thermus chliarophilus, Thermus flavus, Thermus igniterrae, Thermus lacteus, Thermus oshimai, Thermus ruber; Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosipho africanus, Pyrococcus furiosus*(Pfu), *Pyrococcus woesei, Pyrococcus horikoshii, Pyrococcus abyssi, Pyrodictium occultum, Aquifex pyrophilus* and *Aquifex aeolieus*. Most particularly, the template-dependent nucleic acid polymerase is Taq polymerase.

According to one embodiment, the template-dependent nucleic acid polymerase comprises a reverse transcriptase.

According to one embodiment, the template-dependent nucleic acid polymerase in the step (d) is different from the enzyme having the 5' nuclease activity used in the step (b).

According to another embodiment, the template-dependent nucleic acid polymerase in the step (d) is identical to the enzyme having the 5' nuclease activity used in the step (b).

Collectively, the enzyme having the 5' nuclease activity used in the step (b), the template-dependent nucleic acid polymerase used for extension of the upstream primer in the step (b), and the template-dependent nucleic acid polymerase used in the step (d) may be completely or partially identical to or different from one another.

Step (e): Hybridization of First Extended Strand with Second CTO

The first extended strand generated in the step (d) is hybridized with a second CTO (second Capturing and Templating Oligonucleotide).

For hybridization between the first extended strand and the second CTO, the method of the present invention may further comprise denaturing the first extended duplex prior to performing the step (e). During the additional denaturation step, the first extended duplex is dissociated to create an environment in which the first extended strand can be contacted with the second CTO. The denaturation may be carried out by conventional technologies, including, but not limited to, heating, alkali, formamide, urea and glycoxal treatment, enzymatic methods (e.g., helicase action), and binding proteins. For instance, the denaturation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

The most prominent feature of the present invention is to use a second CTO which is distinct from the first CTO, such that a second extended duplex is additionally formed which is distinct from the first extended duplex.

The second CTO used in this step comprises in a 3' to 5' direction (i) a capturing portion comprising a hybridizing nucleotide sequence to the first extended strand and (ii) a templating portion comprising a non-hybridizing nucleotide sequence to the first extended strand (see FIG. 1). Thus, the first extended strand is hybridized with the capturing portion of the second CTO.

The capturing portion of the second CTO serves to hybridize to the first extended strand and the templating portion of the second CTO serves as a template to further extend the first extended strand.

According to an embodiment, the capturing portion of the second CTO comprises a nucleotide sequence identical to all or portion of the nucleotide sequence of the templating portion of the first CTO.

According to an embodiment, the capturing portion of the second CTO comprises a nucleotide sequence identical to all or portion of the nucleotide sequence of the templating portion of the first CTO, and the identical sequence is not present in the templating portion of the second CTO and/or the capturing portion of the first CTO. In other word, the templating portion of the second CTO and/or the capturing portion of the first CTO do not comprise a nucleotide sequence identical to all or portion of the nucleotide sequence of the templating portion of the first CTO.

The term "identical" is used herein to mean that two nucleotides sequences are the same to each other, encompassing the terms "substantially identical" and "perfectly identical". The term "perfectly identical" means that two nucleotide sequences are the same with no exception of any nucleotide, while the term "substantially identical" means that two nucleotide sequences are similar with some different nucleotides (e.g., 1-10, 1-7, 1-5 and 1-3 nucleotide). The term "substantially identical" also means that there are several different nucleotides to the extent that such different nucleotides do not interrupt the hybridization between the first extended strand, particularly the first extended sequence, and a capturing portion of the second CTO. The term "identical" also means that at least 5, 6, 7, 10, 20, 30, 40, 50, 60, 70, 80, 90 or 100 nucleotides are the same between two nucleotide sequences.

Such sequence identity or difference between specific portions of the first CTO and the second CTO allows discrimination between the first CTO and the second CTO.

The first CTO used herein serves to hybridize to and extend the PTO fragment, while the second CTO serves to hybridize to and extend the first extended strand. Thus, the second CTO is distinguished from the first CTO.

The capturing portion of the second CTO used herein can be designed to be hybridized with the various portions of the first extended strand, as follows:

(i) First Embodiment: Hybridization of the Second CTO with the Entire First Extended Strand In a first embodiment, the capturing portion of the second CTO is hybridized with the entire first extended strand consisting of the PTO fragment and the first extended sequence. For this purpose, the capturing portion of the second CTO may be designed to include a hybridizing nucleotide sequence to the entire first extended strand.

According to the first embodiment, the PTO fragment can be hybridized to both the first CTO and the second CTO, so that it can be involved in the formation of the first extended duplex and the second extended duplex.

Since the first embodiment encompasses a process in which the first extended strand is hybridized with the second CTO to generate the second extended duplex, it will be appreciated that the first embodiment falls within the scope of the present invention.

The capturing portion of the second CTO may be designed to have a nucleotide sequence that allow hybridization of the entire PTO fragment but does not allow its extension (for example, by incorporating mismatched nucleotide(s) with the 3'-end part of the PTO fragment).

(ii) Second Embodiment: Hybridization of the Second CTO with a Part of the First Extended Strand (Including a Part of the PTO Fragment)

In a second embodiment, the capturing portion of the second CTO is hybridized with a part of the first extended strand consisting of a part of the PTO fragment and the entire first extended sequence. For this purpose, the capturing portion of the second CTO may be designed to include a hybridizing nucleotide sequence to the part of the PTO fragment and the entire first extended sequence.

The "part of the PTO fragment" which is hybridized with the capturing portion of the second CTO refers to a part, particularly at the 3'-end of the PTO fragment. Depending on the length of the part of the PTO fragment that is hybridized with the capturing portion of the second CTO, the capturing portion of the second CTO may be further hybridized or not hybridized with the PTO fragment itself.

As an example, if the length of the part of the PTO fragment to be hybridized with the capturing portion of the second CTO is long enough such that the PTO fragment itself is hybridized with the capturing portion of the second CTO, the PTO fragment may be involved in hybridization with the second CTO and then formation of the second extended duplex, as in the first embodiment described above.

As another example, if the length of the part of the PTO fragment to be hybridized with the capturing portion of the second CTO is not enough such that PTO fragment itself is not hybridized with the capturing portion of the second CTO, the PTO fragment may not be involved in hybridization with the capturing portion of the second CTO and then formation of the second extended duplex, unlike the first embodiment described above.

The length of the part of the PTO fragment to be hybridized with the capturing portion of the second CTO may be, for example, not less than one nucleotide, not less than two nucleotides, not less than three nucleotides, or not less than four nucleotides. In addition, the length of the part of the PTO fragment to be hybridized with the capturing portion of the second CTO may be, for example, not more than 12 nucleotides, not more than 10 nucleotides, not more than 8 nucleotides, or not more than 6 nucleotides.

(iii) Third Embodiment: Hybridization of the Second CTO with a Part of the First Extended Strand (Excluding the PTO Fragment)

According to a third embodiment, the capturing portion of the second CTO is hybridized with a part of the first extended strand consisting solely of the first extended sequence. For this purpose, the capturing portion of the second CTO may be designed to include a hybridizing nucleotide sequence to the entire first extended sequence.

According to the third embodiment, the PTO fragment is hybridized only with the first CTO to form a first extended duplex, and the first extended strand constituting the first extended duplex is hybridized with the second CTO to form a second extended duplex. The PTO fragments generated in a target-dependent manner are all used to form the first extended strand and the resulting first extended strands are all used to form the second extended duplex, so that the signal from the second extended duplex can be provided without any loss.

(iv) Fourth Embodiment: Hybridization of the Second CTO with a Part of the First Extended Strand (a Part of the First Extended Sequence)

According to a fourth embodiment, the capturing portion of the second CTO is hybridized with a part of the first extended strand consisting solely of a part of the first extended sequence. For this purpose, the capturing portion of the second CTO may be designed to include a hybridizing nucleotide sequence to the part of the first extended sequence.

The "part of the first extension sequence" to be hybridized with the capturing portion of the second CTO includes the 3'-end part of the first extended sequence. The length of the part of the first extended sequence to be hybridized with the capturing portion of the second CTO may be, for example, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 20 nucleotides, 25 nucleotides, 30 nucleotides, or more.

According to the fourth embodiment, the PTO fragment is hybridized only with the first CTO to form a first extended duplex, and the first extended strand constituting the first extended duplex is hybridized with the second CTO to form a second extended duplex. The PTO fragments generated in a target-dependent manner are all used to form the first extended strand and the resulting first extended strands are all used to form the second extended duplex, so that the signal from the second extended duplex can be provided without any loss.

As described above, the capturing portion of the second CTO may have a nucleotide sequence intended for any of the first through fourth embodiments.

Since the first extended strand hybridized to the second CTO is subject to further extension in step (f), the capturing portion of the second CTO needs to be hybridized with the 3'-end part of the first extended strand. According to an embodiment, the capturing portion of the second CTO has at its 5'-end (i) at least a nucleotide complementary to the 3' ultimate nucleotide of the first extended stand; (ii) at least nucleotides complementary to the 3' ultimate nucleotide and the 3' penultimate nucleotide of the first extended strand; or (iii) at least nucleotides complementary to the 3' ultimate nucleotide, the 3' penultimate nucleotide and the 3' antepenultimate nucleotide of the first extended strand.

According to an embodiment, the capturing portion of the second CTO has a non-hybridizing nucleotide sequence to the PTO fragment. According to a particular embodiment, the capturing portion of the second CTO has a nucleotide sequence which is not hybridized with the entire PTO fragment. In other words, the capturing portion of the second CTO comprises a nucleotide sequence to be hybridized with a part of the PTO fragment and the first extended sequence, or comprises a nucleotide sequence to be hybridized with the entire first extended sequence (excluding the PTO fragment) and a part thereof.

According to an embodiment of the present invention, the capturing portion of the second CTO comprises a hybridizing nucleotide sequence to the first extended sequence. In other words, the capturing portion of the second CTO comprises a hybridizing nucleotide sequence to all or part of the first extended sequence.

In addition, the capturing portion of the second CTO has a non-hybridizing nucleotide sequence to a target nucleic acid sequence and oligonucleotides (e.g., the 3'-targeting portion of PTO, the capturing portion of the first CTO, and the tagging portion of the first CTO) used in the methods of the present invention.

The templating portion of the second CTO comprises a non-hybridizing nucleotide sequence to the first extended strand. In an embodiment, the templating portion of the second CTO has a non-hybridizing nucleotide sequence to the first extended strand, so that the first extended strand is not hybridized with the templating portion of the second CTO. In an embodiment, the templating portion of the second CTO has a nucleotide sequence non-complementary to the first extended strand, so that the templating portion of the second CTO is not hybridized to the first extended strand.

In addition, the templating portion of the second CTO has a non-hybridizing nucleotide sequence to a target nucleic acid sequence and oligonucleotides (e.g., the 5'-tagging portion of PTO (or PTO fragment), the 3'-targeting portion of the PTO, the capturing portion of the first CTO, the tagging portion of the first CTO, etc.) used in the methods of the present invention, so that the templating portion of the second CTO is not hybridized to the target nucleic acid sequence and the oligonucleotide.

The templating portion of the second CTO may comprise any sequence so long as it is not hybridized to the portions as described above. Furthermore, the templating portion of the second CTO may comprise any sequence so long as it can serve as a template for further extension of the first extended strand.

The 3'-end of the second CTO may comprise additional nucleotides not involved in hybridization with the first extended strand.

The second CTO may be designed to have a hairpin structure or no hairpin structure.

The length of the second CTO may be widely varied. For example, the second CTO is 5-1000 nucleotides, 5-500 nucleotides, 5-300 nucleotides, 5-100 nucleotides, 5-80 nucleotides, 5-60 nucleotides, 5-40 nucleotides, 7-1000 nucleotides, 7-500 nucleotides, 7-300 nucleotides, 7-100 nucleotides, 7-80 nucleotides, 7-60 nucleotides, 7-40 nucleotides, 15-1000 nucleotides, 15-500 nucleotides, 15-300 nucleotides, 15-100 nucleotides, 15-80 nucleotides, 15-60 nucleotides, 15-40 nucleotides, 20-1000 nucleotides, 20-500 nucleotides, 20-300 nucleotides, 20-100 nucleotides, 20-80 nucleotides, 20-60 nucleotides, 20-40 nucleotides, 30-1000 nucleotides, 30-500 nucleotides, 30-300 nucleotides, 30-100 nucleotides, 30-80 nucleotides, 30-60 nucleotides or 30-40 nucleotides in length.

The capturing portion of the second CTO may have any length so long as it is specifically hybridized with the first extended strand. For example, the capturing portion of the second CTO is 5-100 nucleotides, 5-60 nucleotides, 5-40 nucleotides, 5-30 nucleotides, 5-20 nucleotides, 10-100 nucleotides, 10-60 nucleotides, 10-40 nucleotides, 10-30 nucleotides, 10-20 nucleotides, 15-100 nucleotides, 15-60 nucleotides, 15-40 nucleotides, 15-30 nucleotides or 15-20 nucleotides in length.

The templating portion of the second CTO may have any length so long as it can act as a template in extension of the first extended strand. For example, the templating portion of the second CTO is 1-900 nucleotides, 1-400 nucleotides, 1-300 nucleotides, 1-100 nucleotides, 1-80 nucleotides, 1-60 nucleotides, 1-40 nucleotides, 1-20 nucleotides, 2-900 nucleotides, 2-400 nucleotides, 2-300 nucleotides, 2-100 nucleotides, 2-80 nucleotides, 2-60 nucleotides, 2-40 nucleotides, 2-20 nucleotides, 5-900 nucleotides, 5-400 nucleotides, 5-300 nucleotides, 5-100 nucleotides, 5-80 nucleotides, 5-60 nucleotides, 5-40 nucleotides, 5-30 nucleotides, 10-900 nucleotides, 10-400 nucleotides, 10-300 nucleotides, 15-900 nucleotides, 15-100 nucleotides, 15-80 nucleotides, 15-60 nucleotides, 15-40 nucleotides or 15-20 nucleotides in length.

The 3'-end of the second CTO may have a 3'-OH terminal. Alternatively, the 3'-end of the second CTO is blocked to prohibit its extension. The non-extendible blocking of the second CTO may be achieved in accordance with conventional methods. For instance, the blocking may be performed by adding to the 3'-hydroxyl group of the last nucleotide of the first CTO a chemical moiety such as biotin, labels, a phosphate group, alkyl group, non-nucleotide linker, phosphorothioate or alkane-diol. Alternatively, the blocking may be carried out by removing the 3'-hydroxyl group of the last nucleotide or using a nucleotide with no 3'-hydroxyl group such as dideoxynucleotide.

The second CTO used herein may be hybridized with the undigested PTO depending upon its design scheme. Nevertheless, the 3'-targeting portion of the PTO is not hybridized to the second CTO which prohibits the formation of the second extended duplex.

In the present method, the first CTO competes with the second CTO for hybridization with the first extended strand, which may hinder hybridization between the first extended strand and the second CTO. Namely, the hybridization between the first extended strand and the second CTO may be impeded by the formation of the first extended duplex between the first extended strand and the first CTO. Thus, in order to minimize the interference of hybridization between the first extended strand and the second CTO, the step (e) may be performed under conditions favorable for hybridization of the first extended strand with the second CTO, details of which are described in the section of PCE-IH.

Step (f): Further Extension of First Extended Strand and Formation of Second Extended Duplex The extension reaction is carried out using the resultant of the step (e) and a template-dependent nucleic acid polymerase. The first extended strand hybridized with the capturing portion of the second CTO is further extended to generate a second extended strand comprising a second extended sequence complementary to the templating portion of the second CTO, thereby forming a second extended duplex between the second extended strand and the second CTO.

When the capturing portion of the second CTO comprises a nucleotide sequence to be hybridized with the PTO fragment, the uncleaved PTO may be hybridized to the capturing portion of the second CTO but not extended, resulting in no formation of the second extended duplex; when the capturing portion of the second CTO does not comprise a nucleotide sequence to be hybridized with the PTO fragment, the uncleaved PTO is not hybridized with the second CTO, resulting in no formation of the second extended duplex.

The terms "second extended sequence", "second extended strand" and "second extended duplex" as used in connection with the extension reaction of the first extended strand in step (f) have the following meanings:

As used herein, the term "second extended sequence" refers to a sequence which is newly formed by further extension from the first extended strand in the step (f). In other words, the second extended sequence refers to a portion of the second extended strand as will be described below, excluding the first extended strand.

As used herein, the term "second extended strand" refers to a sequence encompassing the first extended strand and the second extended sequence. In other words, the second extended strand refers to a portion of the second extended duplex as will be described below, excluding the second CTO.

As used herein, the term "second extended duplex" refers to a hybrid or duplex (through complementarity) between the second extended strand and the second CTO. In other words, the second extended duplex means a duplex between the second extended strand, composed of the PTO fragment, the first extended sequence and the second extended sequence, and the second CTO.

It is to be understood that the terms "second extended sequence", "second extended strand" and "second extended duplex" are distinguishable from the terms "first extended sequence", "first extended strand" and "first extended duplex" as described above.

According to an embodiment, the second extended duplex has identical or different $T_m$ value from the first extended duplex.

According to an embodiment, the second extended duplex has a $T_m$ value higher than that of the first extended duplex (e.g., 2° C. or higher, 5° C. or higher, 10° C. or higher, 15° C. or higher, or 20° C. or higher).

According to an embodiment, the second extended duplex has a $T_m$ value lower than that of the first extended duplex (e.g., 2° C. or lower, 5° C. or lower, 10° C. or lower, 15° C. or lower, or 20° C. or lower).

The $T_m$ value of the second extended duplex is adjustable by (i) a sequence and/or length of the first extended strand, (ii) a sequence and/or length of the second CTO, or combination thereof.

For details on the template-dependent nucleic acid polymerase used in step (f), see the disclosure in the step (d).

Step (g): Detection of Presence of Second Extended Strand

Finally, the presence of the second extended strand is detected. The presence of the second extended strand indicates the presence of the target nucleic acid sequence.

The step (g) can be accomplished by detecting a target signal indicative of the presence of a second extended strand.

The term "target signal" as used herein means any signal capable of indicating the presence of the second extended strand. For example, the target signal includes a signal from labels (signal generation or extinguishment), a signal change from labels (signal increase or decrease), a melting curve, a melting pattern and a melting temperature (or $T_m$ value).

The detection of the presence of the second extended strand in the step (g) can be performed by various methods. Several references disclosing the PTOCE method, the PCEC method, the PCE-SH method, the PCE-SC method, the PCE-NH method, or the PCE-IH teaches various label systems and working principles underlying them, which can be applied to the present method for detection of the second extended duplex.

The detection of the presence of the second extended strand in the step (g) can be performed by (i) measuring a signal at a predetermined temperature, or (ii) measuring a signal by melting analysis or a melting followed by hybridization analysis.

According to one embodiment, the detection in step (g) is carried out by measuring a signal indicative of the presence of the second extended strand at a predetermined temperature.

As an example, the presence of the second extended strand is detected by measuring the target signal from the second extended duplex at a predetermined temperature at which the extended duplex maintains its double-stranded form or by measuring the target signal from another duplex between the second extended strand and another oligonucleotide at a predetermined temperature at which the duplex maintains its double-stranded form.

According to an embodiment, the second extended duplex may be detected at a temperature at which the hybrids are partially dissociated. According to an embodiment, the second extended duplex may be detected at a temperature sufficient to dissociate the hybrids to remove the non-target signals.

According to an embodiment, the detection in the step (g) is carried out by measuring a signal indicative of the presence of the second extended strand by a melting analysis or a melting followed by hybridization analysis.

The term used herein "melting analysis" means a method in which a target signal indicative of the presence of the second extended strand is obtained by melting a duplex, including melting curve analysis, melting pattern analysis and melting peak analysis. Particularly, the melting analysis is a melting curve analysis.

According to an embodiment, the detection of the second extended strand in the step (g) is carried out by a melting analysis, in which the second extended duplex is melted to give a target signal indicative of the second extended strand.

According to an embodiment, the detection of the second extended strand in the step (g) is carried out by a melting analysis, in which another duplex between the second extended strand and another oligonucleotide is melted to give a target signal indicative of the presence of the second extended strand.

The term "melting followed by hybridization analysis" as used herein refers to a method of melting the second extended duplex and then hybridizing the melted second extended duplex, to give a target signal indicative of the second extended duplex. Particularly, the melting followed by hybridization analysis is a melting curve analysis.

According to an embodiment, the detection of the second extended strand in the step (g) is carried out by a melting followed by hybridization analysis. Particularly, the detection of the second extended strand in the step (g) is carried out by melting the second extended duplex and hybridizing the resultant at a certain range of temperatures to give a target signal indicative of the second extended strand.

The melting curve or hybridization curve may be obtained by conventional technologies, for example, as described in U.S. Pat. Nos. 6,174,670 and 5,789,167, Drobyshev et al, *Gene* 188: 45(1997); Kochinsky and Mirzabekov *Human Mutation* 19:343(2002); Livehits et al *J. Biomol. Structure Dynam.* 11:783(1994); and Howell et al *Nature Biotechnology* 17:87(1999). For example, a melting curve or hybridization curve may consist of a graphic plot or display of the variation of the output signal with the parameter of hybridization stringency. Output signal may be plotted directly against the hybridization parameter. Typically, a melting curve or hybridization curve will have the output signal, for example fluorescence, which indicates the degree of duplex structure (i.e. the extent of hybridization), plotted on the Y-axis and the hybridization parameter on the X axis.

A plot of the first derivative of fluorescence versus temperature, i.e., a plot of the rate of change in fluorescence vs. temperature (dF/dT vs. T or –dF/dT vs. T) provides a melting peak.

As described above, the detection of the second extended strand at a predetermined temperature or by a melting analysis or a melting followed by hybridization analysis can be carried out in various fashions as follows:

A. Detection of the second extended duplex;
B. Detection of cleavage of the second extended duplex;
C. Detection of the hybrid between the second extended strand and a Signaling Oligonucleotide (SO);
D. Detection of cleavage of the hybrid between the second extended strand and a Signaling Oligonucleotide (SO);
E. Detection of the hybrid between the second CTO and a Hybridizing Oligonucleotide (HO); and
F. Detection of the hybrid between the second extended strand and an Immobilized Oligonucleotide (IO) immobilized on a solid substrate.

The above analyses will be described in detail below.

A. Detection of Second Extended Duplex

According to one embodiment, the detection in the step (g) is carried out based on a PTOCE analysis using a signal from the second extended duplex between the second extended strand and the second CTO (see WO 2012/096523).

According to one embodiment, the second extended strand and the second CTO forms the second extended duplex in the step (f), the second extended duplex provides a detectable signal by (i) at least one label linked to the PTO fragment and/or the second CTO, (ii) a label incorporated into the first extended strand and/or the second extended strand during the extension reaction, (iii) a label incorporated into the first extended strand and/or the second extended strand during the extension reaction and at least one label linked to the second CTO, or (iv) an intercalating label; wherein the presence of the second extended strand is detected by measuring the signal from the second extended duplex.

The labeling systems based on the PTOCE analysis will be described in detail as follows:

(i) At Least One Label Linked to the PTO Fragment and/or the Second CTO

According to an embodiment, the target signal is provided by at least one label linked to the PTO fragment and/or the second CTO.

The label includes an interactive dual label and a single label.

(i-1) Interactive Dual Label

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The donor molecule and the acceptor molecule may be described as a reporter molecular and a quencher molecule in the present invention, respectively. The interactive label system includes a dual label based on "on contact-mediated quenching" (Salvatore et al., Nucleic Acids Research, 2002 (30) no. 21 e122 and Johansson et al., J. AM. CHEM. SOC 2002 (124) pp 6950-6956). The interactive label system includes any label system in which signal change is induced by interaction between at least two molecules (e.g. dye).

Particularly, the signal indicative of the presence of the second extended duplex (i.e., the presence of the target nucleic acid sequence) is generated by interactive label systems, more particularly the FRET label system (i.e., interactive dual label system).

Embodiment I (Intrastrand Interactive-Dual Label)

In an embodiment I of an interactive dual label system, the PTO fragment or the second CTO has an interactive dual label comprising a reporter molecule and a quencher molecule; wherein the hybridization between the first extended strand and the second CTO in the step (e), the formation of the second extended duplex between the second extended strand and the second CTO in the step (f), or the melting of the second extended duplex or the melting followed by hybridization of the second extended duplex induces change of a signal from the interactive dual label to give a detectable signal. The embodiment I is named as an intrastrand interactive-dual label.

Embodiment I-1 (Intrastrand Interactive-Dual Label on the Second CTO)

According to an embodiment I-1, the second CTO has an interactive dual label comprising a reporter molecule and a quencher molecule; wherein the hybridization between the first extended strand and the second CTO in the step (e), the formation of the second extended duplex between the second extended strand and the second CTO in the step (f), or the melting of the second extended duplex or the melting followed by hybridization of the second extended duplex induces change of a signal from the interactive dual label to give a detectable signal.

According to the embodiment I-1, a change in the structural spacing between the reporter molecule and the quencher molecule is induced to give a target signal, upon hybridization between the first extended strand and the second CTO, upon formation of the second extended duplex after further extension of the first extended strand hybridized with the second CTO, or upon melting of the second extended duplex or melting followed by hybridization of the second extended duplex.

For example, prior to hybridization of the first extended strand with the capturing portion of the second CTO, the reporter molecule and the quencher molecule are conformationally adjacent to each other to allow the quencher molecule to quench the signal from the reporter molecule; whereas when the first extended strand hybridized with the second CTO is further extended to form the second extended duplex in the step (f), the reporter molecule and the quencher molecule on the second CTO are conformationally separated to allow the quencher molecule to unquench the signal from the reporter molecule, giving a target signal. In addition, when the second extended duplex is melted, the reporter molecules and the quencher molecules are conformationally adjacent to each other to allow the quencher molecule to quench the signal from the reporter molecule, giving a target signal; when the melted second extended duplex is re-hybridized, the reporter molecule and the quencher molecule are conformationally separated again to allow the quencher molecule to unquench the signal from the reporter molecule, giving a target signal.

The expression used herein "the reporter molecule and the quencher molecule are conformationally adjacent" means that the reporter molecule and the quencher molecule are three-dimensionally adjacent to each other by a conformational structure of the PTO fragment or second CTO such as random coil or hairpin structure.

The expression used herein "the reporter molecule and the quencher molecule are conformationally separated" means that the reporter molecule and the quencher molecule are three-dimensionally separated by change of a conformational structure of the PTO fragment or second CTO upon the formation of a double strand.

According to an embodiment, the reporter molecule and the quencher molecule may be located at any site on the second CTO, so long as the signal from the reporter molecule is quenched and unquenched depending on hybridization between the first extended strand and the second CTO, formation of the second extended duplex, or melting or melting followed by hybridization of the second extended duplex.

According to an embodiment, the reporter molecule and the quencher molecule both are linked to the templating portion of the second CTO.

According to an embodiment, at least one of the reporter molecule and the quencher molecule are linked to the templating portion of the second CTO.

According to an embodiment, at least one of the reporter molecule and the quencher molecule are linked to the capturing portion of the second CTO.

According to an embodiment, the reporter molecule and the quencher molecule are positioned at 5'-end and 3'-end of the second CTO.

According to an embodiment, one of the reporter molecule and the quencher molecule on the second CTO is located at its 5'-end or at 1-5 nucleotides apart from its 5'-end and the other is located to quench and unquench the signal from the reporter molecule depending on conformation of the second CTO.

According to an embodiment, one of the reporter molecule and the quencher molecule on the second CTO is located at its 3'-end or at 1-5 nucleotides apart from its 3'-end and the other is located to quench and unquench the signal from the reporter molecule depending on conformation of the second CTO.

According to an embodiment, the reporter molecule and the quencher molecule are positioned at no more than 80 nucleotides, more particularly no more than 60 nucleotides, still more particularly no more than 30 nucleotides, still much more particularly no more than 25 nucleotides apart from each other. According to an embodiment, the reporter molecule and the quencher molecule are separated by at least 4 nucleotides, more particularly at least 6 nucleotides, still more particularly at least 10 nucleotides, still much more particularly at least 15 nucleotides.

A description of the relative position of the reporter molecule and the quencher molecule on the second CTO can be used to define the position of the intrastrand interactive-dual label on another oligonucleotide.

Depending on the position of the reporter molecule and the quencher molecule on the second CTO, the time at which the signal is generated (i.e., the signal change is caused) may vary.

As an example, when both the reporter molecule and the quencher molecule are located on at the templating portion of the second CTO and the reporter molecule and the quencher molecule are separated enough to unquench the signal from the reporter molecule, the formation of the second extended duplex in the step (f) may give rise to change of a signal from the interactive dual label to provide a detectable signal.

As another example, if both the reporter molecule and the quencher molecule are located on the capturing portion of the second CTO and the reporter molecule and the quencher molecule are separated enough to un quench the signal from the reporter molecule, the hybridization between the first extended strand and the second CTO in the step (e) may give rise to change of a signal from the interactive dual label to provide a detectable signal, and the formation of the second extended duplex in the step (f) maintain the signal.

Embodiment 1-2 (Intrastrand Interactive-Dual Label on the PTO)

According to an embodiment 1-2, the PTO fragment has an interactive dual label comprising a reporter molecule and a quencher molecule; wherein the hybridization between the first extended strand and the second CTO in the step (e), or the melting of the second extended duplex or the melting followed by hybridization of the second extended duplex induces change of a signal from the interactive dual label to give the detectable signal.

In the embodiment 1-2, the capturing portion of the second CTO may comprise a hybridizing nucleotide sequence to the PTO fragment, in order to provide a target signal from the second extended duplex.

According to an embodiment, the reporter molecule and the quencher molecule may be located at any site on the PTO fragment, so long as the signal from the reporter molecule is quenched and unquenched depending on hybridization between the first extended strand and the second CTO or its melting.

According to an embodiment, one of the reporter molecule and the quencher molecule on the PTO fragment is located at its 5'-end or at 1-5 nucleotides apart from its 5'-end and the other is located to quench and unquench the signal from the reporter molecule depending on conformation of the PTO fragment.

In the Embodiment 1-2, where the capturing portion of the second CTO comprises a hybridizing nucleotide sequence to the PTO fragment, a hybrid between the uncleaved PTO and the first CTO as well as a hybrid between the uncleaved PTO and the second CTO may be formed to provide non-target signals. In this case, the measurement of the signals at the temperature at which the hybrid between the uncleaved PTO and the first CTO and the hybrid between the uncleaved PTO and the second CTO are all dissociated, or the difference in $T_m$ values of the second extended duplex and the hybrids permits to discriminate the target signal of the second extended duplex from the non-target signals of the hybrids.

Embodiment II (Interstrand Interactive-Dual Label)

In an embodiment II, the PTO fragment has one of an interactive dual label comprising a reporter molecule and a quencher molecule and the second CTO has the other of the interactive dual label; wherein the hybridization between the first extended strand and the second CTO in the step (e), or the melting of the second extended duplex or the melting followed by hybridization of the second extended duplex induces change of a signal from the interactive dual label to give the detectable signal. The embodiment H is named as an interstrand interactive-dual label.

For example, where the PTO fragment has a quencher molecule and the second CTO has a reporter molecule, the signal from the reporter molecule on the second CTO is not quenched by the quencher molecule on the PTO fragment before the first extended strand is hybridized with the second CTO; whereas when the first extended strand is hybridized with the second CTO in the step (e), the signal from the reporter molecule linked to the second CTO is quenched by the quencher molecule linked to the PTO fragment to provide a target signal. In addition, the formation of the second extended duplex between the second extended strand and the second CTO in the step (f) maintains the signal. Afterwards, when the second extended duplex is melted, the reporter molecules and the quencher molecules are conformationally adjacent to each other to allow the quencher molecule to quench the signal from the reporter molecule, giving a target signal.

The reporter molecule and the quencher molecule may be located at any site of the PTO fragment and the second CTO, so long as the signal from the reporter molecule is quenched by the quencher molecule. It is preferred that the quencher molecule and the reporter molecule is located in close proximity to each other, in order to facilitate the quencher molecule to quench the signal from the reporter molecule upon the hybridization between the first extended strand and the second CTO.

According to an embodiment, the reporter molecule or the quencher molecule on the PTO fragment is located at the 5'-end of the 5'-tagging portion.

According to an embodiment, the reporter molecule or the quencher molecule on the PTO fragment is located at or near the 3'-end of the 5'-tagging portion.

According to an embodiment, the reporter molecule and the quencher molecule are linked to the capturing portion of the second CTO.

According to an embodiment, the reporter molecule and the quencher molecule on the second CTO is located at its 3'-end or at 1-5 nucleotides apart from its 3'-end.

In the Embodiment II, where the capturing portion of the second CTO comprises a hybridizing nucleotide sequence to the PTO fragment, and the reporter molecule and the reporter molecule are adjacent upon the hybridization between the first extended strand and the second CTO, a hybrid between the uncleaved PTO and the second CTO may be formed to provide a non-target signal. In this case, the measurement of the signal at the temperature at which the hybrid between the uncleaved PTO and the second CTO is dissociated, or the difference in $T_m$ values of the second extended duplex and the hybrid permits to discriminate the target signal of the second extended duplex from the non-target signal of the hybrid.

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), Dil (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC(5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Particularly, the reporter molecule and the quencher molecule include JOE, FAM, TAMRA, ROX and fluorescein-based label.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition (Molecular Probes, Eugene, Oreg., 1996) U.S. Pat. Nos. 3,996,345 and 4,351,760.

It is noteworthy that a non-fluorescent black quencher molecule capable of quenching a fluorescence of a wide range of wavelengths or a specific wavelength may be used in the present invention. Examples of those are BHQ and DABCYL.

In the FRET label adopted to the second CTO, the reporter encompasses a donor of FRET and the quencher encompasses the other partner (acceptor) of FRET. For example, a fluorescein dye is used as the reporter and a rhodamine dye as the quencher.

The label may be linked to the second CTO or the PTO (particularly, the tagging portion of the PTO) by conventional methods. Particularly, it is linked to the second CTO or PTO (particularly, the tagging portion of the PTO) through a spacer containing carbon atoms (e.g., 3-carbon spacer, 6-carbon spacer or 12-carbon spacer).

(i-2) Single Label

The present invention is also excellently executed using single label systems for providing signals indicating the presence of target nucleic acid sequences.

According to an embodiment, the PTO fragment or the second CTO has a single label; wherein the hybridization between the first extended strand and the second CTO in the step (e), the formation of the extended duplex between the second extended strand and the second CTO in the step (f), or the melting of the second extended duplex or the melting followed by hybridization of the second extended duplex induces change of a signal from the interactive dual label to give a detectable signal.

Embodiment I (Single Label on the Second CTO)

According to an embodiment I, the second CTO has a single label; wherein the hybridization between the first extended strand and the second CTO in the step (e), the formation of the extended duplex between the second extended strand and the second CTO in the step (f), or the melting of the second extended duplex or the melting followed by hybridization of the second extended duplex induces change of a signal from the single label to give a detectable signal.

In the embodiment I, the fluorescent intensity from the single fluorescent label becomes increased upon hybridization between the first extended strand and the second CTO, upon further extension of the first extended strand hybridized with the second CTO to form the second extended duplex, or upon melting of the second extended duplex or melting followed by hybridization of the second extended duplex, thereby giving a target signal.

According to an embodiment, the single label may be located at any site on the second CTO, so long as the signal intensity from the single label changes depending on hybridization of the first extended strand and the second CTO, formation of the second extended duplex, or melting or melting followed by hybridization of the second extended duplex.

According to an embodiment, the single label is linked to the templating portion or to the capturing portion of the second CTO.

Embodiment II (Simile Label on the PTO)

According to an embodiment II, the PTO fragment has a single label; wherein the hybridization between the first extended strand and the second CTO in the step (e), or the melting of the second extended duplex or the melting followed by hybridization of the second extended duplex induces change of a signal from the single label to give a detectable signal.

In the embodiment II, the capturing portion of the second CTO should comprise a hybridizing nucleotide sequence to the PTO fragment, in order to provide a target signal from the second extended duplex.

According to an embodiment, the single label may be located at any site on the PTO fragment, so long as the signal intensity from the single label changes depending on hybridization of the first extended strand and the second CTO, formation of the second extended duplex, or melting or melting followed by hybridization of the second extended duplex.

The single label used herein has to be capable of providing a different signal depending on its presence on a double strand or single strand. The single label includes a fluorescent label, a luminescent label, a chemiluminescent label, an electrochemical label and a metal label. Particularly, the single label includes a fluorescent label.

The types and preferable binding sites of single fluorescent labels used in this invention are disclosed in U.S. Pat. Nos. 7,537,886 and 7,348,141, the teachings of which are incorporated herein by reference in their entirety. Particularly, the single fluorescent label includes JOE, FAM, TAMRA, ROX and fluorescein-based label. The labeled nucleotide residue is particularly positioned at internal nucleotide residue within the oligonucleotide rather than at the 5'-end or the 3'-end.

The single fluorescent label useful in the present invention may be described with reference to descriptions for reporter and quencher molecules as indicated above.

In particular, where the present invention on a solid phase is performed using a single label, it can utilize a general fluorescent label and does not require a specific fluorescent label capable of providing a fluorescent signal with different intensities depending on its presence on double strand or single strand. The target signal provided on the solid substrate is measured.

When the second CTO immobilized onto a solid substrate is used, chemical labels (e.g. biotin) or enzymatic labels (e.g. alkaline phosphatase, peroxidase, β-galactosidase and β-glucosidase) may be used.

In labeling systems using "a label linked to the PTO fragment and/or the second CTO", the label may be positioned to the extent that when a hybrid between an uncleaved PTO and the first CTO or a hybrid between an uncleaved PTO and the second CTO is formed, the hybrid does not give a non-target signal in the step (e). Alternatively, the label may be positioned to the extent that when a hybrid between an uncleaved PTO and the first CTO or a hybrid between an uncleaved PTO and the second CTO is formed, the hybrid gives a non-target signal in the step (e); wherein the $T_m$ value of the second extended duplex is higher than that of the hybrid between the uncleaved PTO and the first CTO or the hybrid between the uncleaved PTO and the second CTO.

Particularly, where the labels are positioned to the extent that a hybrid between an uncleaved PTO and the first CTO or a hybrid between an uncleaved PTO and the second CTO does not give a non-target signal, the range including $T_m$ value of the hybrid can be utilized to select $T_m$ value of the second extended duplex for detecting a target nucleic acid sequence.

(ii) Label Incorporated into the First Extended Strand and/or the Second Extended Strand During the Extension Reaction The present invention may employ a label incorporated into the first extended strand during the extension reaction of the step (d) for providing a target signal indicative of the presence of the second extended strand.

Alternatively, the present invention may employ a label incorporated into the second extended strand during the extension reaction of the step (f) for providing a target signal indicative of the presence of the second extended duplex.

According to an embodiment, the present invention employs both of a label incorporated into the first extended strand and a label incorporated into the second extended strand.

The phrase "label incorporated into the first extended strand" is used herein to mean a label that is not present on the PTO fragment, but is inserted during extension of the PTO fragment.

The phrase "label incorporated into the second extended strand" is used herein to mean a label that is not present on the first extended strand, but is inserted during further extension of the first extended strand.

The phrase "label incorporated into the second extended duplex" is used herein to mean a label that is inserted during extension of the PTO fragment or during further extension of the first extended strand and is thus present on the resulting second extended duplex.

Although the PTO fragment or the second CTO has no label, a label incorporated into the first extended strand and/or the second extended strand during the extension reaction is successfully used to allow the second extended strand to be labeled.

According to an embodiment, the extension reaction in the step (d) or (f) is performed in the presence of a nucleotide having a single label, thereby incorporating the single label into the first extended strand and/or the second extended strand; wherein the hybridization of the first extended strand with the second CTO, the formation of the second extended duplex between the second extended strand and the second CTO in the step (f), or the melting of the second extended duplex or the melting followed by hybridization of the second extended duplex induces change of a signal from the single label to give the detectable signal.

Details on the signal generating scheme by an incorporating label can be found in the description for the PTO fragment as described above.

According to an embodiment, a nucleotide incorporated during the extension reaction has a first non-natural base and the first CTO or the second CTO has a nucleotide having a second non-natural base with a specific binding affinity to the first non-natural base. Particularly, the nucleotide having the second non-natural base is located at any site on the templating portion of the first CTO or the second CTO.

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns from natural bases as mother compounds, as described, for example, in U.S. Pat. Nos. 5,432,272, 5,965,364, 6,001,983, and 6,037,120. The base pairing between non-natural bases involves two or three hydrogen bonds as natural bases. The base pairing between non-natural bases is also formed in a specific manner.

Specific examples of non-natural bases include the following bases in base pair combinations: iso-C/iso-G, iso-dC/iso-dG, K/X, H/J, and M/N (see U.S. Pat. No. 7,422,850).

For example, the first extended strand is hybridized with the second CTO with a nucleotide having a second non-natural base (e.g., iso-dC) with a specific binding affinity to a first non-natural base (e.g., iso-dG). The extension is carried out in the presence of a nucleotide having the first non-natural base labeled with a single fluorescent label to form the second extended duplex. In the extension reaction, the nucleotide having the first non-natural base is incorporated at an opposition site to the nucleotide having the second non-natural base.

The fluorescent signal from the second extended duplex may be detected on spot of a solid substrate with the immobilized second CTO. When the second extended duplex is melted, a strand having a fluorescent label is released and the fluorescent signal is no longer detected on the spot. Therefore, a signal change can be provided on the spot by melting of the second extended duplex. In this regard, the target signal is given to indicate the presence of the second extended duplex in the step (e).

For types and characteristics of the single labels used, see the section regarding the labeling system using "label linked to the PTO fragment and/or the second CTO" as indicated hereinabove.

(iii) Label Incorporated into the First Extended Strand and/or the Second Extended Strand During the Extension Reaction and at Least One Label Linked to the PTO Fragment or the Second CTO The present invention may employ a labeling system using cooperation of a label incorporated into the first extended strand and/or the second extended strand during the extension reaction and a label linked to the PTO fragment and/or the second CTO.

In an embodiment, the second CTO has one of an interactive dual label comprising a reporter molecule and a quencher molecule, and the extension reaction in the step (d) is performed in the presence of a nucleotide having the other of the interactive dual label, thereby incorporating the label on the nucleotide into the first extended sequence; wherein the hybridization between the first extended strand and the second CTO in the step (e), or the melting of the second extended duplex containing the first extended strand or the melting followed by hybridization induces change of a signal from the interactive dual label to give the detectable signal.

In an embodiment, the second CTO has one of an interactive dual label comprising a reporter molecule and a quencher molecule, and the extension reaction in the step (f) is performed in the presence of a nucleotide having the other of the interactive dual label, thereby incorporating the label into the second extended sequence; wherein the formation of the second extended duplex between the second extended strand and the second CTO in the step (f), or the melting of the second extended duplex or the melting followed by hybridization of the second extended duplex induces change of a signal from the interactive dual label to give the detectable signal.

Particularly, the nucleotide incorporated during the extension reaction has a first non-natural base and the second CTO has a nucleotide having a second non-natural base with a specific binding affinity to the first non-natural base.

The site of the label on the second CTO and the incorporation site of the label incorporated are determined to the extent that the two labels act as an interactive dual label for inducing signal change in the hybridization and melting of the second extended duplex.

Particularly, the templating portion of the second CTO has a reporter or quencher molecule and a nucleotide having a second non-natural base.

(iv) Intercalating Label

The present invention may employ an intercalating label for providing a target signal indicative of the presence of the second extended duplex. The intercalating label is more useful on a solid phase reaction using the immobilized second CTOs because double-stranded nucleic acid molecules present in samples can generate signals.

In an embodiment, the target signal is provided by an intercalating label; wherein the hybridization between the first extended strand and the second CTO in the step (e), the formation of the second extended duplex between the second extended strand and the second CTO in the step (f), or the melting of the second extended duplex or the melting followed by hybridization of the second extended duplex induces change of a signal from the intercalating label to provide a detectable signal.

Exemplified intercalating dyes useful in this invention include SYBR™ Green I, PO-PRO™-1, BO-PRO™-1, SYTO™43, SYTO™44, SYTO™45, SYTOX™Blue, POPO™-1, POPO™-3, BOBO™-1, BOBO™-3, LO-PRO™-1, JO-PRO™-1, YO-PRO™1, TO-PRO™1, SYTO™ 11, SYTO™13, SYTO™15, SYTO™16, SYTO™20, SYTO™23, TOTO™-3, YOYO™3, GelStar™ and thiazole orange. The intercalating dyes intercalate specifically into double-stranded nucleic acid molecules to generate signals.

The embodiment is also applicable to another embodiment using a melting analysis.

In an embodiment, the second extended strand or the second CTO comprises an acceptor of a FRET (fluorescence resonance energy transfer) and the detection is performed in the presence of an intercalating dye. The formation of the second extended duplex between the second extended strand and the second CTO in the step (f), or the melting of the second extended duplex or the melting followed by hybridization of the second extended duplex induces change in signal from the acceptor to provide the detectable signal.

B. Detection of Occurrence of the Cleavage of the Second Extended Duplex

According to an embodiment, the detection of the step (g) is performed based on a PCEC assay using a signal generated from the cleavage of the second extended duplex between the second extended strand and the second CTO (see WO 2012/134195).

According to an embodiment, the second extended duplex comprises a label and a cleavage site for a nucleolytic enzyme, and the second extended duplex provides a detectable signal by the cleavage at the cleavage site; wherein the presence of the second extended strand in the step (g) is detected by cleaving the second extended duplex by the nucleolytic enzyme and measuring a signal generated by the cleavage.

Upon the formation of the second extended duplex, the cleavage site for nucleolytic enzymes is generated. A multitude of nucleolytic enzymes acting specifically on a duplex structure have been known to one of skill in the art.

According to an embodiment, the nucleolytic enzyme is a restriction enzyme, the templating portion of the second CTO comprises a sequence recognized by the restriction enzyme and the formation of the second extended duplex in the step (f) generates a cleavage site of the restriction enzyme. According to an embodiment, the nucleolytic enzyme is a ribonuclease, the templating portion of the second CTO comprises a RNA sequence and the formation of the second extended duplex in the step (f) produces the DNA-RNA hybrid duplex to generate a cleavage site of the ribonuclease. According to an embodiment, the nucleolytic enzyme is a 5' to 3' exonuclease and the formation of the extended duplex in the step (f) generates on the CTO a cleavage site of the 5' to 3' exonuclease.

The PTO fragment, the first extended strand and/or the second CTO may be designed and constructed such that a desired type of cleavage sites for nucleolytic enzymes is introduced.

In the PCEC assay, a detectable signal may be provided by (i) at least one label linked to the PTO fragment and/or the second CTO, (ii) a label incorporated into the first extended strand and/or the second extended strand during the extension reaction, (iii) a label incorporated into the first extended strand and/or the second extended strand during the extension reaction and at least one label linked to the second CTO, or (iv) intercalating label.

For details on the principles of the PCEC assay, see WO 2012/134195. The labeling system based on the PCEC assay will be described as follows:

(i) Single Label

The present invention may provide signal for the occurrence of cleavage of the second extended duplex indicating the presence of the target nucleic acid sequence by use of a single label.

For types and characteristics of the signal labels, see the section of PTOCE assay as described above.

According to an embodiment, the second CTO has the single label, the cleavage of the second extended duplex form a cleaved fragment with the single label, a signal from the single label prior to the cleavage of the second extended duplex is different from a signal from the single label after the cleavage of the second extended duplex, and the difference in signals allow to detect the occurrence of the cleavage of the second extended duplex.

According to an embodiment, the PTO fragment, the first extended strand or the second extended strand has the single label, the cleavage of the second extended duplex form a cleaved fragment with the single label, a signal from the single label prior to the cleavage of the second extended duplex is different from a signal from the single label after the cleavage of the second extended duplex, and the difference in signals allow to detect the occurrence of the cleavage of the second extended duplex.

According to an embodiment, the single label providing differential signals dependent on the cleavage of the second extended duplex is a fluorescent terbium chelate or a single label emitting a polarized fluorescence.

According to an embodiment, the single label is linked to the second CTO, particularly the templating portion of the second CTO, more particularly to the 5'-end of the templating portion of the second CTO.

According to an embodiment, the single label is linked to the PTO, particularly the 5'-tagging portion of the PTO. Particularly, the single label is positioned on the PTO such that the PTO fragment has the single label.

Where the present invention uses the single label, it is preferable that the present invention is performed on a solid phase using immobilized second CTOs. In the case that the present invention employing the single label is performed on a solid phase, the single label linked to either the PTO or the second CTO may provide signal indicating the occurrence of the cleavage of the second extended duplex.

According to an embodiment, the second CTO is immobilized through its 5'-end or its 3'-end onto a solid substrate.

Where the second CTO is immobilized through its 3'-end onto a solid substrate and the single label is used, it is preferable that the single label is linked to the templating portion of the second CTO and the cleavage site for the nucleolytic enzyme is generated for 5' to 3' exonuclease, restriction enzyme or ribonuclease.

As an example, the first extended strand is hybridized with the second CTO immobilized through its 3'-end onto a solid substrate and further extended to form the second extended duplex, thereby generating the cleavage site for 5' to 3' exonuclease. The 5' to 3' exonuclease cleaves the second extended duplex by attacking the cleavage site and releases a fluorescent reporter molecule from the 5'-end of the second CTO. Where the target nucleic acid sequence is present, spots containing immobilized second CTOs are observed to show decrease or extinguishment of fluorescence. In the absence of the target nucleic acid sequence, the decrease or extinguishment of fluorescence in spots containing immobilized second CTOs are not observed.

As a further example, the first extended strand is hybridized with the second CTO (comprising in its templating portion a sequence recognized by the restriction enzyme or RNA molecule) immobilized through its 5'-end or 3'-end onto a solid substrate and further extended to form the second extended duplex, thereby generating the cleavage site for the restriction enzyme. The restriction enzyme cleaves the second extended duplex and releases a fluorescent reporter molecule from the 3'-end or 5'-end of the second CTO. Where the target nucleic acid sequence is present, spots containing immobilized second CTOs are observed to show decrease or extinguishment of fluorescence. In the absence of the target nucleic acid sequence, the decrease or extinguishment of fluorescence in spots containing immobilized second CTOs are not observed.

According to an embodiment, the single label linked to the second CTO is located at its 5'-end or at 1-5 nucleotides apart from its 5'-end. Alternatively, the single label linked to the second CTO is located at its 3'-end or at 1-5 nucleotides apart from its 3'-end.

According to an embodiment, the single label linked to the PTO is located at its 5'-end or at 1-5 nucleotides apart from its 5'-end.

(ii) Interactive Dual Label

The present invention may provide signal for the occurrence of cleavage of the second extended duplex indicating the presence of the target nucleic acid sequence by use of an interactive dual label.

For types and characteristics of the interactive dual labels, see the section of PTOCE assay as described above.

According to an embodiment, the interactive dual label is linked to the second CTO.

According to an embodiment, the cleavage site for the nucleolytic enzyme is positioned between the reporter molecule and the quencher molecule linked to the second CTO, the quencher molecule quenches a signal from the reporter molecule prior to the formation of the second extended duplex, the cleavage of the second extended duplex separates the reporter molecule and the quencher molecule from each other and the occurrence of the cleavage of the second extended duplex is detected by measuring a signal from the label.

The interactive label system in the present invention is useful in a liquid phase and on a solid phase.

Where the interactive label system is employed, it is preferable that the cleavage site generated on the second extended duplex is a cleavage site for 5' to 3' exonuclease, restriction enzyme or ribonuclease.

As an example, the first extended strand is hybridized with the second CTO and further extended to form the second extended duplex, thereby generating the cleavage site for 5' to 3' exonuclease, restriction enzyme or ribonuclease. The cleavage site is positioned between the reporter molecule and the quencher molecule linked to the second CTO.

Prior to the formation of the extended duplex, the quencher molecule is positioned at a site suitable to quench signal from the reporter molecule. Particularly, the quenching occurs when the two labels are adjacent along the length of the second CTO or in a three-dimensional manner by the formation of conformational structures such as random coil and hairpin structure.

The 5' to 3' exonuclease cleaves the 5'-end of the second extended duplex and releases a fluorescent reporter molecule to cause a signal change from fluorescent reporter molecule. The restriction enzyme cleaves the second extended duplex by attacking the cleavage site and releases a fluorescent reporter molecule to cause a signal change from fluorescent reporter molecule. The occurrence of the cleavage of the second extended duplex is detected by measuring the fluorescent signal change for determination of the presence of the target nucleic acid sequence.

Where the quencher molecule is fluorescent, it is preferred that a signal from the quencher molecule is employed to be measured.

According to an embodiment, at least one of the reporter molecule and the quencher molecule is linked to the templating portion of the second CTO, particularly the 5'-end of the second CTO.

According to an embodiment, both the reporter molecule and the quencher molecule are linked to the templating portion of the second CTO.

According to an embodiment, one of the reporter molecule and the quencher molecule is linked to the 5'-end of the second CTO and the other to the 3'-end.

According to an embodiment, either the reporter molecule or the quencher molecule linked to the templating portion of the second CTO is located at its 5'-end or at 1-5 nucleotides apart from its 5'-end. For instance, the quencher molecule may be located at the 5'-end of the templating portion of the second CTO or at 1-5 nucleotides apart from its 5'-end and the reporter molecule may be located at 5-50 nucleotides apart from the quencher molecule.

According to an embodiment, the interactive dual label is located at a suitable position such that the quenching between the interactive dual label is maintained at the formation of the second extended duplex and the unquenching between the interactive dual label is accomplished at release of the label by cleavage of the second extended duplex.

In considering a real-time signal generation during the cleavage of the second extended duplex, it is preferred that the reporter molecule and the quencher molecule are positioned at no more than 25 nucleotides, more particularly no more than 20 nucleotides, still more particularly no more than 15 nucleotides, still much more particularly no more than 10 nucleotides apart from each other. According to an embodiment, the reporter molecule and the quencher molecule are separated by at least 3 nucleotides, particularly at least 4 nucleotides, more particularly at least 5 nucleotides, still more particularly at least 6 nucleotides.

When the second extended duplex is formed, the reporter molecule and the quencher molecule on the second CTO may be conformationally separated to allow the quencher molecule to unquench the signal from the reporter molecule. The cleavage of the second extended duplex completely separates the reporter molecule from the quencher molecule, enabling a signal change by the unquenching to become much higher.

Furthermore, because the cleaved fragment having a label (e.g., reporter molecule) is produced, the occurrence of the cleavage of the second extended duplex may be analyzed by directly detecting a signal from the label linked to the cleaved fragment under more flexible or convenient conditions (e.g., high-stringent conditions or conditions after washing on a solid substrate).

According to an embodiment, one of the interactive dual label linked to the immobilized second CTO is remained on the solid substrate after the cleavage of the second extended duplex.

According to an embodiment, where the second CTO immobilized onto the solid substrate has the interactive dual label and 5' to 3' exonuclease is used as nucleolytic enzymes, one of the interactive dual label may be securely remained on the solid substrate after the cleavage of the second extended duplex by conferring suitable conditions for dissociating a fragment of the second CTO from the second extended duplex or conferring resistance to 5' to 3' exonuclease activities into internal nucleotides of the second CTO.

According to a preferred embodiment, the resistance to 5' to 3' exonuclease activities is conferred by nucleotides having a backbone resistant to the 5' to 3' exonuclease activity, including various phosphorothioate linkages, phosphonate linkages, phosphoroamidate linkages and 2'-carbohydrates modifications, more particularly, phosphorothioate linkage, alkyl phosphotriester linkage, aryl phosphotriester linkage, alkyl phosphonate linkage, aryl phosphonate linkage, hydrogen phosphonate linkage, alkyl phosphoroamidate linkage, aryl phosphoroamidate linkage, phosphoroselenate linkage, 2'-O-aminopropyl modification, 2'-O-alkyl modification, 2'-O-allyl modification, 2'-O-butyl modification, α-anomeric oligodeoxynucleotide and 1-(4'-thio-β-D-ribofuranosyl) modification.

The reporter molecule and the quencher molecule useful in the present invention can be found in the PTOCE assay.

(iii) Intercalating Label

The present invention may employ an intercalating label for association of the cleavage reaction of the second extended duplex and signal generation indicative of the presence of the target nucleic acid sequence.

The intercalating label is more useful on a solid phase reaction using immobilized second CTOs because double-stranded nucleic acid molecules present in samples can generate signals.

According to an embodiment, the second CTO is immobilized through its 5'-end or its 3'-end onto the solid substrate, an intercalating dye is used as a label, the cleavage of the second extended duplex forms a cleaved fragment containing the intercalating dye, the cleaved fragment is released from the solid substrate, thereby inducing a signal change on the solid substrate to provide a signal indicating the occurrence of the cleavage of the second extended duplex. In that case, it is preferable that the cleavage reaction of the second extended duplex is performed using restriction enzymes or RNase.

According to an embodiment, a cleaved fragment not immobilized onto the solid substrate is released from the solid substrate.

Exemplified intercalating dyes useful in this invention can be found in the Section of PTOCE assay.

C. Detection of a Hybrid Between the Second Extended Strand and a Signaling Oligonucleotide (SO)

According to an embodiment, the detection in the step (g) is performed based on a PCE-SH assay using a signal generated from the hybrid between the second extended strand and a Signaling Oligonucleotide (SO) (see WO 2013/115442).

According to an embodiment, the method further uses a Signaling Oligonucleotide (SO); wherein the SO comprises a hybridizing nucleotide sequence to the second extended strand and a label; the SO provides a detectable signal by hybridization with the second extended strand; and the presence of the second extended strand in the step (g) is detected by hybridizing the SO with the second extended strand and measuring the signal generated by the hybridization.

According to an embodiment, the SO comprises a hybridizing nucleotide sequence to the second extended sequence.

In the PCE-SH assay, a detectable signal may be provided by (i) a label linked to the SO, (ii) a combination of a label linked to the SO and a label linked to the PTO fragment, (iii) a combination of a label linked to the SO and a label to be incorporated into the first extended strand and/or the second extended strand during the extension reaction in the step (d) and/or the step (f), or (iv) a combination of a label linked to the SO and an intercalating label.

For details on the principles of the PCE-SH assay, see WO 2012/115442. The labeling system based on the PCE-SH assay will be described as follows:

(i) Single Label Linked to the SO

The present invention may provide signal for formation of the second extended strand indicating the presence of the target nucleic acid sequence using a single label.

According to an embodiment, the SO is labeled with a single label and the hybridization between the SO and the second extended strand induces change in signal from the single label to provide the detectable signal.

For types and characteristics of the single labels, see the section of PTOCE assay as described above.

According to an embodiment, the single label on the SO is located at 1-15 nucleotide, 1-10 nucleotide or 1-5 nucleotide apart from its 5'-end or its 3'-end. More particularly, the single label is located at the middle portion of SO.

(ii) Intrastrand Interactive-Dual Label Linked to SO

For types and characteristics of the intrastrand interactive dual labels, see the section of PTOCE assay as described above.

According to an embodiment, the SO is labeled with an interactive dual label comprising a reporter molecule and a quencher molecule and the hybridization between the SO and the second extended strand induces change of a signal from the interactive dual label to provide a detectable signal. Prior to hybridization of the SO, the reporter molecule and the quencher molecule on the SO are conformationally adjacent to each other to allow the quencher molecule to quench the signal from the reporter molecule. Upon hybridization, the reporter molecule and the quencher molecule on the SO are conformationally separated to allow the quencher molecule to unquench the signal from the reporter molecule, causing change of a signal from the interactive dual label.

According to an embodiment, the reporter molecule and the quencher molecule are positioned at the 5'-end (or 3'-end) and 3'-end (or 5'-end) of the SO. According to an embodiment, one of the reporter molecule and the quencher molecule on the SO is located at its 5'-end or at 1-5 nucleotides apart from its 5'-end and the other is located to quench and unquench the signal from the reporter molecule depending on conformation of SO.

According to an embodiment, one of the reporter molecule and the quencher molecule on the SO is located at its 3'-end or at 1-5 nucleotides apart from its 3'-end and the other is located to quench and unquench the signal from the reporter molecule depending on conformation of the SO.

(iii) Interstrand Interactive-Dual Label

In the embodiment using the interstrand interactive-dual label, the second extended strand has one of an interactive dual label comprising a reporter molecule and a quencher molecule and the SO has the other of the interactive dual label.

According to an embodiment, the SO comprises one label among a reporter molecule and a quencher molecule of an interactive dual label, and the second extended strand comprises the other label among the reporter molecule and the quencher molecule which is originated from the PTO fragment, incorporated into the first extended strand during extension reaction, or incorporated into second extended strand during extension reaction; wherein the hybridization between the SO and the second extended strand induces change in signal from the interactive dual label to provide the detectable signal.

An incorporation of label into a first extended strand or a second extended strand can be performed as described herein.

A label linked to the SO may be either a reporter molecule or a quencher molecule, and a label to the PTO fragment may be either a quencher molecule or a reporter molecule.

The label may be linked to any site (e.g., the 5'-end of the SO) on the SO, so long as it interacts with the label on the second extended strand upon hybridization with the second extended strand to induce change in signals.

(iv) Interactive-Dual Label Using Two SOs

In the embodiment of the interactive-dual label using two SOs, the method of the present invention uses an additional SO comprising a complementary sequence to the second extended strand, the two SOs are hybridized with the second extended strand in an adjacent manner, the two SOs each comprises one label among a reporter molecule and a quencher molecule of an interactive dual label; and the hybridization between the two SOs and the second extended strand induces change in signal from the interactive dual label to provide the detectable signal.

Particularly, at least one of the two SOs comprises a portion hybridized to the second extended sequence newly generated in the extension reaction of the step (f).

According to an embodiment, the two SOs may be hybridized with any sites of the second extended strand so long as their hybridization with the extended strand permits the quencher molecule to quench the signal from the reporter molecule. Particularly, the two SOs are positioned in an immediately adjacent manner or 1-5 nucleotides apart from each other.

According to an embodiment, where the two SOs may be adjacently hybridized with the second extended strand, the reporter molecule and the quencher molecule may be linked to any sites of the two SOs so long as the quencher molecule quenches the signal from the reporter molecule. For example, the reporter molecule or the quencher molecule is linked to the 5'-end of one SO or 1-5 nucleotides apart from its 5'-end, and the quencher molecule or the reporter molecule to the 3'-end of the other SO or 1-5 nucleotides apart from its 3'-end.

(v) FRET Label Using Intercalating Dyes

According to the present invention, a FRET (fluorescence resonance energy transfer) signaling becomes practical using intercalating dyes.

According to an embodiment, the SO comprises an acceptor of a FRET and the hybridization in the step (e) is performed in the presence of an intercalating dye; wherein the hybridization between the SO and the first extended strand induces change in signal from the acceptor of the SO to provide the detectable signal, and the extension of the first extended strand maintains the signal.

D. Detection of Cleavage of a Hybrid Between the Second Extended Duplex and a Signaling Oligonucleotide (SO)

According to an embodiment, the detection in the step (g) is performed by a PCE-SC assay using a signal from the cleavage of the hybrid between the second extended strand and a Signaling Oligonucleotide (SO) (see WO 2013/157821)

According to an embodiment, the method further uses a Signaling Oligonucleotide (SO); wherein the SO comprises a hybridizing nucleotide sequence to the second extended strand and a label; wherein a hybrid between the SO and the second extended duplex comprises a cleavage site for a nucleolytic enzyme; wherein the hybrid provides a detectable signal by the cleavage at the cleavage site; wherein the presence of the second extended strand in the step (g) is detected by cleaving the hybrid using the nucleolytic enzyme and measuring the signal generated from the cleavage.

In the PCE-SC assay, the hybrid between the SO and the second extended strand comprises a cleavage site for an interactive dual label comprising a reporter molecule and a quencher molecule, or a single label, a 5' to 3' exonuclease, a ribonuclease or a restriction enzyme; wherein the cleavage of the SO and the second extended strand induce change of a signal from the interactive dual label or the single label, providing a detectable signal.

For details on the principles of the PCE-SC assay, see WO 2013/157821. The labeling system based on the PCE-SC assay will be described as follows:

(i) Interactive Dual Label

For types and characteristics of the interactive dual labels, see the section of PTOCE assay as described above.

According to an embodiment of this invention, the signal indicative of the occurrence of the cleavage of the second extended strand/SO hybrid (i.e., the presence of the target nucleic acid sequence) is generated by interactive label systems, particularly the FRET label system (i.e., interactive dual label system).

According to an embodiment, the SO has an interactive dual label comprising a reporter molecule and a quencher molecule, the cleavage site for the nucleolytic enzyme is positioned between the reporter molecule and the quencher molecule linked to the SO, the cleavage of the SO of the second extended strand/SO hybrid separates the reporter molecule and the quencher molecule from each other and the occurrence of the cleavage reaction of the SO of the second extended strand/SO hybrid is detected by measuring a signal from the label.

In certain embodiment, prior to the formation of the second extended strand/SO hybrid, the quencher molecule is positioned at a site suitable to quench signal from the reporter molecule.

The interactive label system in the present invention is useful in a liquid phase and on a solid phase.

Where the interactive label system is employed, the cleavage site generated is a cleavage site for 5' nuclease, restriction enzyme or ribonuclease.

The nucleolytic enzyme (e.g., 5' nuclease) may cleave a 5'-end portion of the SO of the second extended strand/SO hybrid to release the reporter molecule, thereby inducing signal change from the reporter molecule. The occurrence of the cleavage of the second extended strand/SO hybrid may be detected by measuring the fluorescent signal for determination of the presence of the target nucleic acid sequence.

According to an embodiment, at least one of the reporter molecule and the quencher molecule is linked to the 5'-end of the SO. In certain embodiment, one of the reporter molecule and the quencher molecule is linked to the 5'-end of the SO and the other to the 3'-end.

According to an embodiment, one of the reporter molecule and the quencher molecule on the SO is located at its 5'-end or at 1-10 nucleotides apart from its 5'-end and the other is located to quench the signal from the reporter molecule before the hybridization of SO with the second extended strand.

According to an embodiment, one of the reporter molecule and the quencher molecule on the SO is located at its 3'-end or at 1-10 nucleotides apart from its 3'-end and the other is located to quench and the signal from the reporter molecule before the hybridization of SO with the second extended strand.

For instance, the reporter molecule on the SO may be located at the 5'-end or at 1-5 nucleotides apart from its 5'-end and the quencher molecule may be located at 5-80 nucleotides apart from the reporter molecule.

According to an embodiment, the interactive dual label is located at sites sufficient to maintain quenching phenomenon prior to the formation of the second extended strand/SO hybrid, and induce unquenching upon the cleavage of the second extended strand/SO hybrid.

Considering real-time signal generation during the cleavage of the second extended strand/SO hybrid, the reporter molecule and the quencher molecule may be positioned at no more than 80 nucleotides, no more than 60 nucleotides, no more than 30 nucleotides, no more than 25 nucleotides, no more than 20 nucleotides, no more than 15 nucleotides, or no more than 10 nucleotides apart from each other. According to an embodiment, the reporter molecule and the quencher molecule may be separated by at least 3 nucleotides, at least 4 nucleotides, at least 5 nucleotides, at least 6 nucleotides, at least 10 nucleotides or at least 15 nucleotides.

Furthermore, because the cleaved fragment having a label (e.g., reporter molecule) is produced, the occurrence of the cleavage of the second extended strand/SO hybrid may be analyzed by directly detecting a signal from the label linked to the cleaved fragment under more flexible or convenient conditions (e.g., high-stringent conditions or conditions after washing on a solid substrate).

According to an embodiment, one of the interactive dual label linked to the immobilized SO is remained on the solid substrate after the cleavage of the second extended strand/SO hybrid.

According to an embodiment, where the SO immobilized onto the solid substrate has the interactive dual label and 5' nuclease is used as nucleolytic enzymes, one of the interactive dual label may be securely remained on the solid substrate after the cleavage of the second extended strand/SO hybrid by conferring to suitable conditions for dissociating a fragment of the SO from the hybrid or conferring resistance to 5' nuclease activities into internal nucleotides of the SO (e.g., nucleotides having a backbone resistant to the 5' to 3' exonuclease activity or nucleotides having a label on its base).

Where the SO comprises the 5'-tagging portion non-complementary to the second extended strand, either reporter or quencher molecule may be positioned on the 5'-tagging portion considering the cleavage site.

(ii) Single Label

The present invention is also excellently executed using single label systems for providing signals for the occurrence of the second extended strand/SO hybrid indicating the presence of target nucleic acid sequences.

For types and characteristics of the single labels, see the section of PTOCE assay as described above.

In an embodiment of the present invention, the SO has a single label, the cleavage of the SO of the second extended strand/SO hybrid produces a fragment having the single label, and the occurrence of the cleavage of the SO of the second extended strand/SO hybrid is detected by detecting the release of the single-labeled fragment. In such case, a signal from the single label prior to the cleavage of the SO is different from a signal from the single label after the cleavage of the SO, and the difference in signals permits to detect the occurrence of the cleavage of the SO of the second extended strand/SO hybrid.

According to an embodiment, the single label is linked to the 5'-end or the 3'-end of the SO.

Where the present invention uses the single label, the present invention is efficiently performed on a solid phase using immobilized SOs. According to an embodiment, the SO is immobilized through its 5'-end or its 3'-end onto a solid substrate.

According to an embodiment, the SO is immobilized on the surface of a solid substrate via its 3'-end or 5'-end, the SO has a single label, the cleavage of the SO of the second extended strand/SO hybrid produces a fragment having the single label, and the fragment is released on the solid substrate, whereby a signal change occurs on the solid substrate to detect the occurrence of the cleavage of the SO of the second extended strand/SO hybrid.

Where the SO is immobilized through its 3'-end onto the solid substrate, the single label is linked to the 5'-end of the SO and the cleavage site generated in the step (e) is that for 5' nuclease, restriction enzyme or ribonuclease.

In certain embodiment, the single label on the SO is located at the 5'-end or at 1-5 nucleotides apart from the 5'-end. Alternatively, the single label is located at the 3'-end or at 1-5 nucleotides apart from the 3'-end of the SO.

E. Detection of a Hybrid Between the Second CTO and a Hybridizing Oligonucleotide (HO)

According to an embodiment, the detection in the step (g) is performed by a PCE-NH using a signal generated from the hybrid between the second CTO and a Hybridizing Oligonucleotide (HO) (see WO 2014/104818).

According to an embodiment, the method further uses a Hybridizing Oligonucleotide (HO); wherein the HO comprises a hybridizing nucleotide sequence to the second CTO and a label; wherein a hybrid between the HO and the second CTO provides a detectable signal; wherein the presence of the second extended strand in the step (g) is detected by measuring the signal from the hybrid; wherein the presence of the signal from the hybrid indicates the absence of the second extended strand.

In the PCE-NH assay, a detectable signal may be provided by (i) a label linked to the HO, (ii) a label linked to the second CTO, (iii) a combination of a label linked to the HO and a label linked to the second CTO, and (iv) an intercalating label.

For details on the principles of the PCE-NH assay, see WO 2014/104818. The labeling system based on the PCE-NH assay will be described as follows:

(i) Single Label Linked to HO or Second CTO

The present invention can provide a signal indicative of the absence of the target nucleic acid sequence, by hybridizing a HO having a single label with the second CTO, or by hybridizing a HO with the second CTO having a single label.

According to an embodiment, it is necessary to detect the signal at a temperature to allow hybridization between the HO and the second CTO.

(ii) Interactive Dual Label Linked to HO or Second CTO

According to an embodiment, a detectable signal is provided by an interactive dual label linked to the HO or the second CTO.

Specifically, the first extended strand is hybridized with the second CTO. Then, the HO labeled with an interactive dual label comprising a reporter molecule and a quencher molecule is hybridized with the templating portion of the second CTO. Afterwards, the first extended strand is further extended to induces the cleavage of the HO to separate the reporter molecule from the quencher molecule, thereby providing a signal indicative of the presence of the second extended strand.

In such embodiment, where the dual label-linked nucleotides are relatively adjacent, a change between signals prior to cleavage of the HO and signals post to cleavage of the HO can be used for signal detection.

Where the dual label-linked nucleotides are relatively apart, the hybridization between the HO and the second CTO induces the conformational separation of the interactive dual label to unquench the signal from the reporter molecule, even if the HO is not cleaved, thereby providing signal changes. In this case, the signal from the cleaved fragment of HO may be detected at a higher temperature (e.g., 95° C.) at which the hybridization between the HO and the second CTO is prevented.

According to an embodiment, the reporter molecule and the quencher molecule may be located at any site on the HO, so long as the cleaved HO and uncleaved HO provide distinct signals.

In certain embodiment, the reporter molecule and the quencher molecule each is located at both ends of the HO.

(iii) Interactive Dual Label Linked to HO and Second CTO

According to an embodiment, a detectable signal is provided by an interactive dual label comprising a reporter molecule and a quencher molecule, one linked to the HO and the other linked to the second CTO.

In certain embodiment, when the HO is hybridized to the second CTO, the reporter molecule and the quencher molecule are located on the HO and second CTO such that the signal from the reporter molecule is quenched by the quencher molecule. Cleavage of the HO induced by further extension of the first extended strand releases HO from the second CTO and separates the reporter molecule from the quencher molecule so that the quencher molecule unquenches the signal from the reporter molecule, thereby providing a signal indicative of the presence of the second extended strand.

According to an embodiment, it is necessary to detect the signal at a temperature to allow hybridization between the HO and the second CTO.

According to one embodiment, the HO can be designed to have a hairpin structure.

In certain embodiments, one of the reporter molecule and the quencher molecule is linked to the 3'-end of HO and the other to the 5'-end of the second CTO.

According to an embodiment, a label system such as an interactive dual label with two HOs, can be used in the method of the present invention. The interactive dual label may be located at any site on the two HOs, as long as the cleaved HO and uncleaved HO provide distinguishable signals. The types and positions of the labels can be found in the label system using SO as described above.

According to an embodiment, a labeling system such as FRET using an intercalating dye can be used in the method of the invention. The FRET label may be located at any site on the two HOs, as long as the cleaved HO and uncleaved HO provide distinguishable signals.

F. Detection of a Hybrid Between the Second Extended Strand and an Immobilized Oligonucleotide (IO)

According to an embodiment, the detection in the step (g) is performed by a PCE-IH assay using a signal generated from the hybrid between the second extended strand and the IO (Immobilized Oligonucleotide) (see WO 2015/008985).

According to an embodiment, the method further uses an Immobilizing Oligonucleotide (IO) immobilized on a solid substrate; wherein the IO comprises a hybridizing nucleotide sequence to the second extended strand; wherein the second extended strand comprises a label; wherein the IO provides a detectable signal by the hybridization with the second extended strand; wherein the presence of the second extended strand in the step (g) is detected by hybridizing the IO with the second extended strand and measuring a signal generated by the hybridization.

In the PCE-IH assay, a detectable signal is provided by (i) a label linked to the PTO fragment, (ii) a label to be incorporated into the first extended strand and/or the second extended strand during the extension reaction of the step (d) or step (f), or (iii) a combination of a label incorporated into the first extended strand and/or the second extended strand during the extension reaction of the step (d) or (f) and a label linked to the PTO fragment.

For details on the principles of the PCE-IH assay, see WO 2015/008985. The labeling system based on the PCE-IH assay will be described as follows:

(i) Single Label Linked to PTO Fragment

The present invention may provide a signal for the presence of the second extended strand indicating the presence of the target nucleic acid sequence by using the single label. The PTO fragment labeled with a single label is hybridized with the first CTO and extended on the first CTO to produce the first extended strand. The first extended strand is hybridized with the second CTO and further extended on the second CTO to produce the second extended strand, whereby the single label is contained in the second extended strand. Afterwards, the second extended strand is hybridized with the IO immobilized on a solid substrate to provide a detectable signal on the solid substrate, followed by detection of the signal indicative of the presence of the second extended strand.

For types and characteristics of the signal labels, see the section of PTOCE assay as described above.

According to an embodiment, the single label on the PTO may be located at any site so long as the PTO fragment is ensured to contain the single label. According to an embodiment, the single label on the PTO may be located at any site of the 5'-tagging portion, for example, the 5'-end of the 5'-tagging portion.

(ii) Label to be Incorporated into the First Extended Strand and/or the Second Extended Strand During the Extension Reaction According to an embodiment, the label used in this invention is the label to be incorporated into the first extended strand and/or the second extended strand, the templating portion of the first CTO or the second CTO comprises a nucleotide containing a second non-natural base, and the extension reaction of the step (d) or the step (f) is performed in the presence of a nucleotide containing a label and a first non-natural base with a specific binding affinity to the second non-natural base, thereby incorporating the label into the first extended strand and/or the second extended strand. Afterwards, the second extended strand is hybridized with the IO immobilized on the solid substrate to provide a detectable signal on the solid substrate and the signal indicative of the presence of the second extended strand is then detected.

(iii) Combination of the Single Label of the PTO Fragment and the Label to be Incorporated into the First Extended Strand and/or the Second Extended Strand According to an embodiment, the label used in this invention is a combination of the single label linked to the PTO fragment and the label to be incorporated into the first extended strand and/or the second extended strand during the extension reaction, and the single label and the incorporated label are an interactive dual label containing a pair of an acceptor and a donor.

As an example, the PTO comprising the 5'-tagging portion labeled with a fluorescent single label (donor) is hybridized with the target nucleic acid sequence and then cleaved. The PTO fragment containing the fluorescent single label (donor) is hybridized with the first CTO containing iso-dC and iso-dG labeled with an acceptor is incorporated into an opposite site to iso-dC during the extension reaction to introduce the acceptor into the first extended strand, thereby forming an interactive dual label on the first extended strand. Then, the first extended strand is hybridized with the second CTO and further extended to produce the second extended strand. Afterwards, the second extended strand is hybridized with the IO immobilized on the solid substrate and irradiated using an excitation light for the donor to elicit energy transfer from the donor to the acceptor, thereby inducing signal change from the acceptor and providing a detectable signal on the solid substrate.

As another example, the PTO comprising the 5'-tagging portion labeled with a fluorescent single label (donor) is hybridized with the target nucleic acid sequence and then cleaved. The PTO fragment containing the fluorescent single label (donor) is hybridized with the first CTO and extended to form the first extended strand. The first extended strand is hybridized with the second CTO containing iso-dC and iso-dG labeled with an acceptor is incorporated into an opposite site to iso-dC during the extension reaction to introduce the acceptor into the second extended strand, thereby forming an interactive dual label on the second extended strand. Afterwards, the second extended strand is hybridized with the IO immobilized on the solid substrate and irradiated using an excitation light for the donor to elicit energy transfer from the donor to the acceptor, thereby inducing signal change from the acceptor and providing a detectable signal on the solid substrate.

(iv) Intercalating Dyes

According to an embodiment, the hybridization between the second CTO and the IO is performed in the presence of an intercalating dye, the label contained in the second extended strand is an acceptor to receive signal from the intercalating dye, the signal from the intercalating dye intercalated into a hybrid between the second extended strand and the IO is transferred to the acceptor, and the acceptor provides the detectable signal.

For example, the PTO comprising the 5'-tagging portion labeled with a fluorescent label (acceptor) is hybridized with the target nucleic acid sequence and then cleaved. The PTO fragment containing the fluorescent label (acceptor) is hybridized with the first CTO and extended to form the first extended strand. Then the first extended strand is hybridized with the second CTO, and extended to form the second extended strand. Afterwards, the second extended strand is hybridized with the IO immobilized on the solid substrate in the presence of an intercalating dye as a donor to intercalate the intercalating dye into the hybrid. Following irradiation by using an excitation light for the donor, the energy transfer is elicited from the donor to the acceptor, thereby inducing signal change from the acceptor and providing a detectable signal on the solid substrate.

Alternatively, with no use of the label contained in the second extended strand, the hybridization between the second extended strand and the IO may be performed in the presence of an intercalating dye and signal from the intercalating dye intercalated into a hybrid between the second extended strand the IO is detected to analyze the presence of the target nucleic acid sequence.

According to one embodiment, the step (e) is carried out under conditions which is favorable for hybridization of the first extended strand in a single-stranded form with the second CTO, and the inhibition of hybridization between the first extended strand and the second CTO by the formation of the first extended duplex between the first extended strand and the first CTO is prevented.

According to an embodiment, the condition favorable for hybridizing the first extended strand in a single-stranded form with the second CTO is a condition for increasing the number of first extended strands in a single-stranded form in the step (e).

According to an embodiment, the condition for increasing the number of first extended strands in a single-stranded form in the step (e) may be one for denaturing the first extended duplex prior to hybridization between the first extended strand and the second CTO. Such denaturation increases the chance of contact between the first extended strand in a single-stranded form and the second CTO, thereby producing an increased number of the hybrids between the first extended strand and the second CTO. In certain embodiments, the method of the present invention further comprises denaturing the first extended duplex prior to hybridization between the first extended strand and the second CTO.

According to an embodiment, the condition for increasing the number of first extended strands in a single-stranded form in the step (e) may be one for eliminating the first CTO prior to hybridization between the first extended strand and the second CTO. For example, a biotinylated CTO may be eliminated via specific affinity to streptavidin or avidin. In one embodiment, the method further comprises eliminating the first CTO prior to hybridization between the first extended strand and the second CTO.

In certain embodiments, the elimination of the first CTO is carried out in a vessel different from that used for hybridization between the first extended strand and the second CTO.

Alternatively, the condition for increasing the number of first extended strands in a single-stranded form in step (e) is to use the PTO and the first CTO at a molar ratio of greater than 1 (specifically, greater than 1.2, greater than 1.3, greater than 1.5, greater than 1.8, greater than 2, greater than 3, greater than 4, greater than 5, greater than 7, or greater than 10). By controlling the molar ratio, the number of first extended strands which are present in a single-stranded form without forming a first extended duplex with the first CTO will be increased.

The present inventors have made efforts to improve the detection efficiency of the method of the present invention and obtained the following results: The amount of the first CTOs remains constant during the entire reaction of the method of the present invention, while the first extended strand is generated in a dependent manner on the presence of the target nucleic acid sequence. As the number of first extended strands increases, the number of first extended strands in a single-stranded form that are not hybridized to the first CTO becomes increased. Therefore, the inhibition by the first CTO on the hybridization between the first extended strand and the second CTO can be excluded as much as possible, and sufficient hybridization between the first extended strand and the second CTO occurs, resulting in improved detection efficiency of the method of the present invention.

Considering the cleavage efficiency of the PTO, the hybridization efficiency between the PTO fragment and the first CTO, and the extension efficiency of the PTO fragment, it is preferred that the amount of the PTO is higher than that of the first CTO. When the amount (i.e., molar ratio) of PTO vs. the first CTO is adjusted, the method of the present invention may further comprise repeating all or a portion of steps (a)-(g). For example, when steps (a)-(d) are repeated with denaturation, only the first extended strand is repeatedly produced without changing the amount of the first CTO. As such, the first extended strand may be produced in a more efficiently produced, the first extended strand in a single-stranded state may become more dominant, and the number of first extended strands may be greater than the first CTO. In one embodiment, the repetition step involving denaturation may comprise at least denaturing the extended duplex. Other components (e.g., upstream oligonucleotides, downstream primers, and enzymes) may be used in sufficient amounts so as not to be limiting factors.

The method of increasing the number of the first extended strands can be equally applied to the PCE-SH analysis described above.

The PTO, first CTO, second CTO, and optionally SO, HO and IO may be comprised of naturally occurring dNMPs. Alternatively, the PTO, first CTO, second CTO, and optionally SO, HO and IO may be comprised of modified nucleotide or non-natural nucleotide such as PNA (peptide nucleic acid, see PCT Publication No. WO 92/20702) and LNA (locked nucleic acid, see PCT Publication Nos. WO 98/22489, WO 98/39352 and WO 99/14226). The PTO, first CTO, second CTO, and optionally SO, HO and IO may comprise universal bases such as deoxyinosine, inosine, 1-(2'-deoxy-beta-D-ribofuranosyl)-3-nitropyrrole and 5-nitroindole. The term "universal base" refers to one capable of forming base pairs with each of the natural DNA/RNA bases with little discrimination between them.

As described above, the PTO may be cleaved at a site located in a 3'-direction apart from the 3'-end of the 5'-tagging portion of the PTO. The cleavage site may be located at the 5'-end part of the 3'-targeting portion of the PTO. Where the PTO fragment comprises the 5'-end part of the 3'-targeting portion of the PTO, a site of the first CTO hybridized with the 5'-end part of the 3'-targeting portion may comprise a universal base, degenerate sequence or their combination. For instance, if the PTO is cleaved at a site located one nucleotide in a 3'-direction apart from the 3'-end of the 5'-tagging portion of the PTO, it is advantageous that the 5'-end part of the capturing portion of the first CTO comprises a universal base for hybridization with the nucleotide. If the PTO is cleaved at a site located two nucleotides in a 3'-direction apart from the 3'-end of the 5'-tagging portion of the PTO, it is advantageous that the 5'-end of the capturing portion of the first CTO comprises a degenerate sequence and its 3'-direction-adjacent nucleotide comprises a universal base. As such, where the cleavage of the PTO occurs at various sites of the 5'-end part of the 3'-targeting portion, the utilization of universal bases and degenerate sequences in the first CTO is useful. In addition, where the PTOs having the same 5'-tagging portion are used for screening multiple target nucleic acid sequences under upstream primer extension-dependent cleavage induction, the PTO fragments having different 5'-end parts of the 3'-targeting portion may be generated. In such cases, universal bases and degenerate sequences are usefully employed in the first CTO. The strategies using universal bases and degenerate sequences in the first CTO ensure to use one type or minimal types of the first CTO for screening multiple target nucleic acid sequences.

In a particular embodiment, the first CTO comprises a set of the first CTO having G (guanine) at the 5'-end of the capturing portion, the first CTO having C (cytosine) at the 5'-end of the capturing portion, the first CTO having A (adenine) at the 5'-end of the capturing portion, and the first CTO having T (thymine) at the 5'-end of the capturing portion.

In a particular embodiment, the first CTO comprises a set of the first CTO having G (guanine) at the 5'-end of the capturing portion and the first CTO having C (cytosine) at the 5'-end of the capturing portion.

In a particular embodiment, the first CTO further comprises the first CTO having another degenerate base at the 5'-end of the capturing portion in said set.

According to a particular embodiment, the method further comprises repeating all or a portion of the steps (a)-(g) with denaturation between repeating cycles. This repetition permits to amplify the target nucleic acid sequence and/or the target signal.

According to an embodiment, the method further comprises melting the second extended duplex or melting the second extended duplex followed by hybridization after the step (g) to provide a detectable signal; wherein the presence of the second extended strand is detected again by measuring the signal.

The denaturation may be carried out by conventional technologies, including, but not limited to, heating, alkali, formamide, urea and glycoxal treatment, enzymatic methods (e.g., helicase action), and binding proteins. For instance, the denaturation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

The detection of the step (g) may be performed in a real-time manner, an end-point manner, or a predetermined time interval manner. Where the present invention further comprises repeating the steps (a)-(g), it is preferred that the signal detection is performed for each cycle of the repetition at a predetermined temperature (i.e. real-time manner), at the end of the repetition at a predetermined temperature (i.e. end-point manner) or at each of predetermined time intervals during the repetition at a predetermined temperature. Preferably, the detection may be performed for each cycle of the repetition in a real-time manner to improve the detection accuracy and quantification.

In the repetition, where an upstream primer is used as an upstream oligonucleotide, the method of the present invention is performed in the presence of a downstream primer, particularly by a PCR method.

According to an embodiment, the steps (a)-(g) are performed in a reaction vessel or some of the steps (a)-(g) are performed in separate reaction vessels.

The present invention does not require that target nucleic acid sequences to be detected and/or amplified have any particular sequence or length, including any DNA (gDNA and cDNA) and RNA molecules.

Where a mRNA is employed as starting material, a reverse transcription step is necessary prior to performing annealing step, details of which are found in Joseph Sambrook, et al., Molecular Cloning, A Laboratory Manual, Cold Spring Harbor Laboratory Press, Cold Spring Harbor, N.Y. (2001); and Noonan, K. F. et al., Nucleic Adds Res. 16:10366 (1988). For reverse transcription, a random hexamer or an oligonucleotide dT primer hybridizable to mRNA can be used.

The target nucleic acid sequences which may be detected and/or amplified include any naturally occurring prokaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The present invention is also useful in detection of a nucleotide variation. Particularly, the target nucleic acid sequence comprises a nucleotide variation. The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term "nucleotide variation" used herein includes any variation at a particular location in a nucleic acid sequence. In other words, the term "nucleotide variation" includes a wild type and its any mutant type at a particular location in a nucleic acid sequence.

In the present invention for detection of a nucleotide variation in a target nucleic acid sequence, where primers or probes used have a complementary sequence to the nucleotide variation in the target nucleic acid sequence, the target nucleic acid sequence containing the nucleotide variation is described herein as a matching template. Where primers or probes used have a non-complementary sequence to the nucleotide variation in the target nucleic add sequence, the target nucleic acid sequence containing the nucleotide variation is described herein as a mismatching template.

For detection of nucleotide variations, the 3'-end of the upstream primer may be designed to be opposite to a site of a nucleotide variation in a target nucleic acid sequence. According to a preferred embodiment, the 3'-end of the upstream primer has a complementary sequence to the nucleotide variation in a target nucleic acid sequence. The 3'-end of the upstream primer having a complementary sequence to the nucleotide variation in the matching template and extended to induce cleavage of the PTO. The resultant PTO fragment is hybridized with the first CTO, and then the first extended strand is hybridized with the second CTO to provide the target signal. In contrast, where the 3'-end of the upstream primer is mismatched to a nucleotide variation in a mismatching template, it is not extended under conditions that annealing of the 3'-end of primers is essential for extension even when the upstream primer is hybridized with the mismatching template, thereby resulting in no generation of the target signal.

Alternatively, it is possible to use PTO cleavage depending on the hybridization of PTO having a complementary sequence to a nucleotide variation in a target nucleic acid sequence. For example, under controlled conditions, a PTO having a complementary sequence to the nucleotide variation in the target nucleic acid sequence is hybridized with the matching template and then cleaved. The resultant PTO fragment is hybridized with the first CTO to produce the first extended strand, and the first extended strand is hybridized with the second CTO to provide the target signal. While, under the controlled conditions, the PTO is not hybridized with a mismatching template having non-complementary sequence in the nucleotide variation position and not cleaved. Particularly, in this case, the complementary sequence to the nucleotide variation in the PTO is positioned at its middle of the 3'-targeting portion of the PTO.

Alternatively, it is preferable that the 5'-end part of the 3'-targeting portion of the PTO is positioned to a nucleotide variation in a target nucleic acid sequence for the detection of the nucleotide variation and the 5'-end part of the 3'-targeting portion of the PTO has a complementary sequence to the nucleotide variation in a target nucleic acid sequence.

In an embodiment for the detection of a single nucleotide variation, the 5'-end of the 3'-targeting portion of the PTO has a complementary sequence to the single nucleotide variation in a target nucleic acid sequence. As described above, the cleavage of the PTO hybridized with a matching template may be induced at a site immediately adjacent in a 3'-direction to the 5'-end of the 3'-targeting portion of the PTO, for example, under upstream primer extension-dependent cleavage induction. The 3'-end of the PTO fragment has the complementary nucleotide to the single nucleotide variation. The PTO fragment is hybridized with a first CTO having a capturing portion comprising a sequence corresponding to the nucleotide variation and then extended to form the first extended strand, and the first extended strand is hybridized with the second CTO and extended to form the second extended duplex, providing the target signal.

If the same PTO is hybridized with a mismatching template having the identical sequence to the matching template except for the single nucleotide variation, the cleavage of the PTO may occur at a site two nucleotides apart in a 3'-direction from the 5'-end of the 3'-targeting portion of the PTO. The 3'-end of the PTO fragment has the further cleaved nucleotide than the complementary nucleotide to the single nucleotide variation. Where the site of the first CTO hybridized with the additional-cleaved nucleotide is designed to have a non-complementary sequence to the further cleaved nucleotide, the 3'-end of the PTO fragment is not hybridized with the first CTO, resulting in no extension of the PTO fragment in a controlled condition. Even if the PTO fragment is extended to form the first extended duplex and then the second extended duplex, the duplexes has different $T_m$ values from the duplex derived from hybridization between the PTO and the mismatching template.

According to a preferred embodiment, a cleavage site of the PTO having a complementary sequence to the nucleotide variation at its 5'-end part of the 3'-targeting portion is different depending on hybridization with a matching template or with a mismatching template, such that the PTO fragment released from either hybridization event has different sequence particularly, in its 3'-end part, more particularly, in its 3'-end.

According to a preferred embodiment, the selection of the nucleotide sequence of first CTO in consideration of the difference in 3'-end parts of the PTO fragments allows to discriminate the matching template from the mismatching template.

According to a preferred embodiment, the target nucleic acid sequence used in the present invention is a pre-amplified nucleic acid sequence. The utilization of the pre-amplified nucleic acid sequence permits to significantly increase the sensitivity and specificity of target detection of the present invention.

According to a preferred embodiment, the method is performed in the presence of a downstream primer.

The advantages of the present invention may be highlighted in the simultaneous (multiplex) detection of at least two target nucleic acid sequences.

According to a preferred embodiment, the method is performed to detect at least two types (more particularly, at least three types, still more particularly at least five types) of target nucleic acid sequences.

According to a preferred embodiment, the method is performed to detect at least two types (more particularly, at least three types, still more particularly at least five types) of target nucleic acid sequences; wherein the upstream oligonucleotide comprises at least two types (more particularly at least three types, still more particularly at least five types) of oligonucleotides, the PTO comprises at least two types (more particularly at least three types, still more particularly at least five types) of the PTOs, the first CTO comprises at least one type (particularly at least two types, more particularly at least three types, still more particularly at least five types) of the first CTOs, and the second CTO comprises at least one type (particularly at least two types, more particularly at least three types, still more particularly at least five types) of the second CTOs. Optionally, where SO, HO, and/or IO are used, the SO, HO, and/or IO comprises at least two types (particularly at least three types, more particularly at least five). When at least two types of the target nucleic acid sequences are present, the method provides at least two types of the target signals corresponding to the at least two types of the target nucleic acid sequences.

The 5'-tagging portions of the at least two PTOs may have an identical sequence to each other. For instance, where the present invention is carried out for screening target nucleic acid sequences, the 5'-tagging portions of PTOs may have the identical sequence.

Furthermore, a single type of the first CTO may be used for detection of a plurality of target nucleic acid sequences. For example, where the PTOs having an identical sequence in their 5'-tagging portions are employed for screening target nucleic acid sequences, a single type of the first 00 may be used.

In addition, the method of the present invention can use a single type of the 5'-tagging portion of the PTO, i.e., the 5'-tagging portion having the same sequence, for the detection of a plurality of target nucleic acid sequences. Namely, the sequence of the 5'-tagging portion may be determined to have an arbitrary sequence irrespective of the target nucleic acid sequences to be detected, facilitating the design of the PTO.

Furthermore, the method of the present invention can use a single type of the second CTO, i.e., having the same sequence, for the detection of a plurality of target nucleic acid sequences. For example, if the capturing portion of the second CTO is designed to hybridize only to the first extended sequence in the first extended strand, the second CTO may be used to detect a variety of target nucleic acid sequences. As such, the second CTO used in the method of the present invention can be prepared in advance regardless of the type of target nucleic acid sequences, the use of the second CTO as a universal oligonucleotide will allow for simple and cost-effective target detection.

According to an embodiment, the first extended duplexes corresponding to the at least two types of the target nucleic acid sequences have different $T_m$ values from each other.

According to an embodiment, the second extended duplexes corresponding to the at least two types of the target nucleic acid sequences have different $T_m$ values from each other.

According to an embodiment, the at least two types of the target signals corresponding to the at least two types of the target nucleic acid sequences are provided from different types of labels from each other.

According to a preferred embodiment, the at least two types of the target signals corresponding to the at least two types of the target nucleic acid sequences are provided from the same type of labels.

According to a preferred embodiment, the at least two type of the target signals corresponding to the at least two types of the target nucleic acid sequences are provided from the same type of labels; wherein the first extended duplexes or the second extended duplexes corresponding to the at least two types of the target nucleic acid sequences have different $T_m$ values from each other.

The term used herein "different types of labels" refers to labels with different characteristics of detectable signals. For example, FAM and TAMRA as fluorescent reporter labels are considered as different types of labels because their excitation and emission wavelengths are different from each other.

Where the present invention is performed to simultaneously detect at least two types of the target nucleic acid sequences by melting curve analysis and the second extended duplexes corresponding to the at least two types of the target nucleic acid sequences have different $T_m$ values from each other, it is possible to detect at least two types of the target nucleic acid sequences even using a single type of a label (e.g. FAM).

As such, if one or more target nucleic acid sequence is intended for detection in one tube, the method of the present invention can be used for detection of at least one target nucleic acid sequence.

Target Detection Using Immobilized Oligonucleotide on a Solid Phase

The prominent advantage of the present invention is to be effective in detection of target nucleic acid sequences even on a solid phase such as microarray.

According to an embodiment, the second CTO is immobilized through its 5'-end or 3'-end onto a solid substrate.

For the solid phase reaction, the second CTO is immobilized directly or indirectly (particularly indirectly) through its 5'-end or 3'-end (particularly the 3'-end) onto the surface of the solid substrate. Furthermore, the second CTO may be immobilized on the surface of the solid substrate in a covalent or non-covalent manner. Where the immobilized second CTOs are immobilized indirectly onto the surface of the solid substrate, suitable linkers are used. The linkers useful in this invention may include any linkers utilized for probe immobilization on the surface of the solid substrate. For example, alkyl or aryl compounds with amine functionality, or alkyl or aryl compounds with thiol functionality serve as linkers for second CTO immobilization. In addition, poly (T) tail or poly (A) tail may serve as linkers.

According to an embodiment, the solid substrate used in the present invention is a microarray. The microarray to provide a reaction environment in this invention may include any those known to one of skill in the art. All processes of the present invention, i.e., hybridization to target nucleic acid sequences, cleavage, extension, melting and fluorescence detection, are carried out on the microarray. The immobilized second CTOs on the microarray serve as hybridizable array elements. The solid substrate to fabricate microarray includes, but not limited to, metals (e.g., gold, alloy of gold and copper, aluminum), metal oxide, glass, ceramic, quartz, silicon, semiconductor, Si/SiO$_2$ wafer, germanium, gallium arsenide, carbon, carbon nanotube, polymers (e.g., polystyrene, polyethylene, polypropylene and polyacrylamide), sepharose, agarose and colloids. A plurality of immobilized second CTOs in this invention may be immobilized on an addressable region or two or more addressable regions on a solid substrate that may comprise 2-1,000,000 addressable regions. Immobilized second CTOs may be fabricated to produce array or arrays for a given application by conventional fabrication technologies such as photolithography, ink-jetting, mechanical microspotting, and derivatives thereof.

According to an embodiment, the second CTO immobilized on the solid substrate comprises an interactive dual label.

In the present invention, the PTO fragment is produced by cleavage of the PTO hybridized with the target nucleic acid sequence, the PTO fragment is extended on the first CTO to produce the first extended strand, and the first extended strand is further extended on the second CTO to produce the second extended strand.

To increase the number of the second extended strand, additional PTOs may be used which produce additional fragments extendable on the first CTO by 5' nuclease cleavage of the PTOs. The manner in which additional PTOs are used to generate additional fragments may vary.

In an embodiment, the additional PTO comprises (i) a 3'-targeting portion comprising a hybridizing nucleotide sequence to the templating portion of the first CTO and (ii) a 5'-tagging portion comprising a non-hybridizing nucleotide sequence to the templating portion of the first CTO and a hybridizing nucleotide sequence to the capturing portion of the tagging portion of the first CTO. In this embodiment, the additional PTO is located downstream of the PTO fragment that is hybridized with the capturing portion of the first CTO. The PTO fragments are extended to cleave the additional PTO and the cleavage produces additional PTO fragment.

In one embodiment, the additional PTO comprises (i) a 3'-targeting portion comprising a hybridizing nucleotide sequence to the templating portion of the second CTO and (ii) a 5'-tagging portion comprising a non-hybridizing nucleotide sequence to the templating portion of the second CTO and a hybridizing nucleotide sequence to the capturing portion of the tagging portion of the first CTO. In this embodiment, the additional PTO is located downstream of the first strand that is hybridized with the second CTO. The first extended strand is extended to cleave the additional PTO and the cleavage produces additional PTO fragment.

According to one embodiment of the solid-phase method, the present invention uses a Signaling Oligonucleotide (SO), and the SO is immobilized on a solid substrate through its 5'-end or 3'-end.

According to one embodiment of the solid phase method, the present invention uses a Hybridizing Oligonucleotide (HO), and the HO is immobilized on a solid substrate through its 5'-end or 3'-end.

According to one embodiment of the solid-phase method, the present invention uses an Immobilized Oligonucleotide (IO) immobilized on a solid substrate and the second CTO can be immobilized through the IO without being immobilized directly on a solid substrate. In this case, the second CTO additionally comprises an IO-hybridizing portion comprising a hybridizing nucleotide sequence to the IO. In this embodiment, the IO-hybridizing portion may be located at the 3'- or 5'-end of the second CTO. In addition, when the IO-hybridizing portion is located at the 5'-end of the second CTO, the second CTO may additionally comprises a blocker portion between the templating portion of the second CTO and the IO-hybridizing portion, in order to prevent extension of the first extended strand For details of embodiment using the hCTO, see WO 2015/057008, which is incorporated herein by reference in its entirety.

In particular, when the present invention is carried out on a solid phase using a single label, the single label requires no specific characteristics. For the solid phase reactions, any single label can be used.

The method of the present invention may further comprise detecting a target signal from the first extended duplex.

In one embodiment, the method is carried out in the presence of a label to allow the first extended duplex to additionally comprise at least one label, and further comprises detecting a target signal provided by the first extended duplex. The embodiment allows the first extended duplex to provide a target signal as well as the second extended duplex and detects signals provided from both the first extended duplex and the second extended duplex.

For details on labels on the first extended duplex and their signal generation systems, see the description of the second extended duplex. It would be appreciated by those skilled in the art that a signal from the first extended duplex can be generated and detected by various methods, such as the PTOCE method, the PCEC method, the PCE-SH method, the PCE-SC method, the PCE-NH method, or the PCE-IH.

The generation and detection of signals from both the first extended duplex and the second extended duplex as described above can increase the intensity of the target signal compared to that from the second extended duplex only.

II. Detection of Target Nucleic Acid Sequence by PTOCE-E Using Labeling System on the First Extended Duplex In another aspect of the present invention, there is provided a method for detecting a target nucleic acid sequence from a DNA or a mixture of nucleic acids by a PTOCE-E (PTO Cleavage and Extension-dependent Extension) assay, comprising:

(a) hybridizing the target nucleic acid sequence with an upstream oligonucleotide and a PTO (Probing and Tagging Oligonucleotide); wherein the upstream oligonucleotide comprises a hybridizing nucleotide sequence to the target nucleic acid sequence; wherein the PTO comprises (i) a 3'-targeting portion comprising a hybridizing nucleotide sequence to the target nucleic acid sequence and (ii) a 5'-tagging portion comprising a non-hybridizing nucleotide sequence to the target nucleic acid sequence; wherein the 3'-targeting portion of the PTO is hybridized with the target nucleic acid sequence and the 5'-tagging portion of the PTO is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity to release a PTO fragment comprising the 5'-tagging portion or a part of the 5'-tagging portion of the PTO;

(c) hybridizing the PTO fragment with a first CTO (Capturing and Templating Oligonucleotide); wherein the first CTO comprises in a 3' to 5' direction (i) a capturing portion comprising a hybridizing nucleotide sequence to the PTO fragment and (ii) a templating portion comprising a non-hybridizing nucleotide sequence to the 5'-tagging portion and the 3'-targeting portion of the PTO; wherein the PTO fragment is hybridized with the capturing portion of the first CTO;

(d) performing an extension reaction using the resultant of the step (c) and a template-dependent nucleic acid polymerase; wherein the PTO fragment hybridized with the capturing portion of the first CTO is extended to generate a first extended strand comprising a first extended sequence complementary to the templating portion of the first CTO, thereby forming a first extended duplex between the first extended strand and the first CTO;

(e) hybridizing the first extended strand with a second CTO; wherein the second CTO comprises in a 3' to 5' direction (i) a capturing portion comprising a hybridizing nucleotide sequence to the first extended strand and (ii) a templating portion comprising a non-hybridizing nucleotide sequence to the first extended strand; wherein the first extended strand is hybridized with the capturing portion of the second CTO;

(f) performing an extension reaction using the resultant of the step (e) and a template-dependent nucleic acid polymerase; wherein the first extended strand hybridized with the capturing portion of the second CTO is further extended to generate a second extended strand comprising a second extended sequence complementary to the templating portion of the second CTO, thereby forming a second extended duplex between the second extended strand and the second CTO; and (g) detecting the presence of the first extended strand; whereby the presence of the first extended strand indicates the presence of the target nucleic acid sequence.

The first aspect of the present invention is characterized by measuring a signal generated from the second extended duplex to detect the presence of the second extended strand; whereas the second aspect of the present invention is characterized by measuring a signal generated from the first extended duplex to detect the presence of the first extended strand.

Since the second aspect of the present invention is the same as the first aspect except that the first extended duplex provides a signal instead of the second extended duplex, the common descriptions between them are omitted in order to avoid undue redundancy leading to the complexity of this specification.

As one example, the first extended duplex provides a detectable signal by (i) at least one label linked to the PTO fragment and/or the first CTO, (ii) a label incorporated into the first extended duplex during the extension reaction, (iii) a label incorporated into the first extended duplex during the extension reaction and at least one label linked to the first CTO, or (iv) an intercalating label, wherein the presence of the first extended strand is detected by measuring the signal from the first extended duplex.

It would be appreciated by those skilled in the art that a signal from the first extended duplex can be generated and detected by various methods, such as the PTOCE method, the PCEC method, the PCE-SH method, the PCE-SC method, the PCE-NH method, or the PCE-IH.

III. Detection of Target Nucleic Acid Sequence by PTOCE-E Using PTO Containing a Cleavage Site.

In still another aspect of the present invention, there is provided a method for detecting a target nucleic acid sequence from a DNA or a mixture of nucleic acids by a PTOCE-E (PTO Cleavage and Extension-dependent Extension) assay, comprising:

(a) hybridizing the target nucleic acid sequence with a PTO (Probing and Tagging Oligonucleotide) and a reverse primer; wherein the PTO comprises (i) a 3'-targeting portion comprising a hybridizing nucleotide sequence to the target nucleic acid sequence and (ii) a 5'-tagging portion comprising a non-hybridizing nucleotide sequence to the target nucleic acid sequence and a cleavage site for a restriction enzyme, an RNase, or a endonuclease; wherein the 3'-targeting portion of the PTO is hybridized with the target nucleic acid sequence and the 5'-tagging portion of the PTO is not hybridized with the target nucleic acid sequence;

(b) extending the PTO and the reverse primer along the target nucleic acid sequence and cleaving the PTO at the cleavage site by the restriction enzyme, the RNase, or the endonuclease to release a PTO fragment comprising the 5'-tagging portion or a part of the 5'-tagging portion of the PTO;

(c) hybridizing the PTO fragment with a first CTO (Capturing and Templating Oligonucleotide); wherein the first CTO comprises in a 3' to 5' direction (i) a capturing portion comprising a hybridizing nucleotide sequence to the PTO fragment and (ii) a templating portion comprising a non-hybridizing nucleotide sequence to the 5'-tagging portion and the 3'-targeting portion of the PTO; wherein the PTO fragment is hybridized with the capturing portion of the first CTO;

(d) performing an extension reaction using the resultant of the step (c) and a template-dependent nucleic acid polymerase; wherein the PTO fragment hybridized with the capturing portion of the first CTO is extended to generate a first extended strand comprising a first extended sequence complementary to the templating portion of the first CTO, thereby forming a first extended duplex between the first extended strand and the first CTO;

(e) hybridizing the first extended strand with a second CTO; wherein the second CTO comprises in a 3' to 5' direction (i) a capturing portion comprising a hybridizing nucleotide sequence to the first extended strand and (ii) a templating portion comprising a non-hybridizing nucleotide sequence to the first extended strand; wherein the first extended strand is hybridized with the capturing portion of the second CTO;

(f) performing an extension reaction using the resultant of the step (e) and a template-dependent nucleic add polymerase; wherein the first extended strand hybridized with the capturing portion of the second CTO is further extended to generate a second extended strand comprising a second extended sequence complementary to the templating portion of the second CTO, thereby forming a second extended duplex between the second extended strand and the second CTO; and (g) detecting the presence of the first extended strand; whereby the presence of the first extended strand indicates the presence of the target nucleic acid sequence.

Since the method of this section III is characterized by using a PTO having a cleavage site at its 5'-tagging portion, instead of the PTO described in section I above, the common descriptions between them are omitted in order to avoid undue redundancy leading to the complexity of this specification.

This method does not require an upstream oligonucleotide because the PTO serves as a forward primer; while it requires a reverse primer to make a single-stranded 5'-tagging portion of the PTO into a double strand (to form a cleavage site).

In one embodiment, the cleavage site is one recognizable by a restriction enzyme, an RNase, or an endonuclease. Where the cleavage site is one for a restriction enzyme, the site may be one for a restriction enzyme selected from the group consisting of Pho I, PspGI, BstNI, TfiI, ApeKI, TspMI, BstBI, BstEII, BstNI, BstUI, BssKI, BstYI, TaqI, MwoI, TseI, Tsp45I, Tsp509I, TspRI, Tth111I, Nb.BsmI, Nb.BsrDI, Nt.BspQI, Nt.BstNBI and Nick restriction enzyme.

In one embodiment, the extension of the PTO, the reverse primer, the PTO fragment, and the first extended strand is carried out by a nucleic acid polymerase.

The PTO and the reverse primer hybridized with the target nucleic acid sequence are extended along the target nucleic acid sequence, making the 5'-tagging portion of the PTO into a double strand. The double stranded 5'-tagging portion of the PTO is cleaved at the cleavage site by the restriction enzyme, the RNase, or the endonuclease to release a PTO fragment comprising the 5'-tagging portion or a part of the 5'-tagging portion of the PTO. The resulting PTO fragment is involved in a series of steps of hybridization with the first CTO, formation of the first extended duplex, hybridization with the second CTO, and formation of the second extended duplex as described above.

Details of the generation of a fragment due to cleavage at the cleavage site can be found in the Korean Patent Application Publication No. 10-2017-0121700.

IV. Kits for Target Detection

In further aspect of this invention, there is provided a kit for detecting a target nucleic acid sequence from a DNA or a mixture of nucleic acids by a PTOCE-E (PTO Cleavage and Extension-dependent Extension) assay, comprising:

(a) an upstream oligonucleotide comprising a hybridizing nucleotide sequence to the target nucleic acid sequence;

(b) a PTO (Probing and Tagging Oligonucleotide); wherein the PTO comprises (i) a 3'-targeting portion comprising a hybridizing nucleotide sequence to the target nucleic acid sequence and (ii) a 5'-tagging portion comprising a non-hybridizing nucleotide sequence to the target nucleic add sequence; wherein the 3'-targeting portion of the PTO is hybridized with the target nucleic acid sequence and the 5'-tagging portion of the PTO is not hybridized with the target nucleic acid sequence; the upstream oligonucleotide is located upstream of the PTO; wherein the upstream oligonucleotide or its extended strand induces cleavage of the PTO by the enzyme having the 5' nuclease activity to release a PTO fragment comprising the 5'-tagging portion or a part of the 5'-tagging portion of the PTO;

(c) a first CTO (Capturing and Templating Oligonucleotide); wherein the first CTO comprises in a 3' to 5' direction (i) a capturing portion comprising a hybridizing nucleotide sequence to the PTO fragment and (ii) a templating portion comprising a non-hybridizing nucleotide sequence to the 5'-tagging portion and the 3'-targeting portion of the PTO; wherein the PTO fragment is hybridized with the capturing portion of the first CTO; the PTO fragment hybridized with the capturing portion of the first CTO is extended to generate a first extended strand comprising a first extended sequence complementary to the templating portion of the first CTO, thereby forming a first extended duplex between the first extended strand and the first CTO; and (d) a second CTO; wherein the second CTO comprises in a 3' to 5' direction (i) a capturing portion comprising a hybridizing nucleotide sequence to the first extended strand and (ii) a templating portion comprising a non-hybridizing nucleotide sequence to the first extended strand; wherein the first extended strand hybridized with the capturing portion of the second CTO is further extended to generate a second extended strand comprising a second extended sequence complementary to the templating portion of the second CTO, thereby forming a second extended duplex between the second extended strand and the second CTO.

Since the kit of this invention is constructed to perform the detection method of the present invention described above, the common descriptions between them are omitted in order to avoid undue redundancy leading to the complexity of this specification.

According to one embodiment, the PTO, the first CTO, or the second CTO has a single label or an interactive dual label. According to one embodiment, if the first CTO has a label, the second CTO has no label; if the second CTO has a label, the first CTO has no label.

According to one embodiment, the kit further comprises (i) a label incorporated into the first extended duplex and/or the second extended duplex during the extension reaction, or (ii) an intercalating label.

According to one embodiment, the kit further comprises an enzyme having a 5' nuclease activity and a template-dependent nucleic acid polymerase or a template-dependent nucleic acid polymerase having a 5' nuclease activity.

According to one embodiment, the enzyme having a 5' nuclease activity and the template-dependent nucleic acid polymerase are identical to each other.

According to one embodiment, the kit is used for detection of at least two types of nucleic acid sequences, the upstream oligonucleotide comprises at least two types of oligonucleotides, the PTO comprises at least two types of the PTO, the first CTO comprises at least one type of the first CTO, and the second CTO comprises at least one type of the second CTO.

According to one embodiment, the second CTO is immobilized through its 5'-end or 3'-end onto a solid substrate.

According to one embodiment, the kit further comprises a downstream primer.

In still further aspect of this invention, there is provided a kit for detecting a target nucleic acid sequence from a DNA or a mixture of nucleic acids, comprising a second CTO (Capturing and Templating Oligonucleotide), comprising in a 3' to 5' direction:

(i) a capturing portion comprising a hybridizing nucleotide sequence to a first extended strand; and (ii) a templating portion comprising a non-hybridizing nucleotide sequence to the first extended strand;

wherein the first extended strand is formed by cleaving a PTO (Probing and Tagging Oligonucleotide) hybridized with the target nucleic acid sequence with the enzyme having the 5' nuclease activity to release a PTO fragment, hybridizing the PTO fragment with the capturing portion of a first CTO, and extending the PTO fragment by the template-dependent nucleic acid polymerase;

wherein the PTO comprises (i) a 3'-targeting portion comprising a hybridizing nucleotide sequence complementary to the target nucleic acid sequence, and (ii) a 5'-tagging portion comprising a nucleotide sequence non-complementary to the target nucleic acid sequence;

wherein the first CTO (Capturing and Templating Oligonucleotide) comprises in a 3' to 0.5' direction (i) a capturing portion comprising a hybridizing nucleotide sequence to the PTO fragment and (ii) a templating portion comprising a non-hybridizing nucleotide sequence to the 5'-tagging portion and the 3'-targeting portion of the PTO.

In one embodiment, the kit further comprises the first CTO.

According to one embodiment, the first CTO and/or the second CTO have a single label or an interactive dual label.

In a particular embodiment, the first CTO comprises a set of the first CTO having G (guanine) at the 5'-end of the capturing portion, the first CTO having C (cytosine) at the 5'-end of the capturing portion, the first CTO having A (adenine) at the 5'-end of the capturing portion, and the first CTO having T (thymine) at the 5'-end of the capturing portion.

In a particular embodiment, the first CTO comprises a set of the first CTO having G (guanine) at the 5'-end of the capturing portion and the first CTO having C (cytosine) at the 5'-end of the capturing portion.

In a particular embodiment, the first CTO further comprises the first CTO having another degenerate base at the 5'-end of the capturing portion in said set.

All of the present kits described hereinabove may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity. The kits may also include reagents necessary for performing positive and negative control reactions. Optimal amounts of reagents to be used in a given reaction can be readily determined by the skilled artisan having the benefit of the current disclosure. The kits, typically, are adopted to contain the constituents aforedescribed in separate packaging or compartments.

The features and advantages of this invention will be summarized as follows:

(a) According to the present invention, a probing and tagging oligonucleotide (PTO) hybridized with a target nucleic acid sequence is cleaved to release a PTO fragment, the PTO fragment is hybridized with a first Capturing and Templating Oligonucleotide (first CTO) to form a first extended strand, and the first extended stand is hybridized with a second CTO to provide a second extended strand which is produced in a target-dependent manner.

(b) The presence of the second extended strand can be detected using a signal provided from the second extended duplex or additional oligonucleotides to detect the presence of the second extended strand. The presence of the second extended strand can be determined by a variety of methods or processes such as a melting curve analysis and detection at a predetermined temperature (e.g. a real-time manner and end-point manner).

(c) The PTOCE method developed by the present inventor provides a signal upon extension of the PTO fragment along the CTO. However, when the PTO hybridized with a non-target nucleic acid sequence, rather than a target nucleic acid sequence, may be cleaved, the PTO fragment may be hybridized with and extended along the CTO, resulting in a false positive signal (e.g., SNP assay using PTOCE). In contrast, according to the PTOCE-E method of the present invention, the first extended strand which is generated by extension of the PTO fragment on the first CTO does not provide a signal, but the second extended strand which is generated using another CTO (second CTO) provides a signal. In this case, the use of appropriate amounts of the first CTO and the second CTO can prevent the formation of the second extended duplex from a small amount of the first extended strand (false positive strand) produced by a non-target nucleic acid sequence, consequently reducing the occurrence of a false positive signal.

(d) The PCE-SH method developed by the present inventors may exhibits a decreased signal by competition of a labeled probe (i.e., SO) with a CTO for hybridization with the extended strand. In contrast, according to the PTOCE-E method of the present invention, the first extended strand not only hybridizes to the second CTO but also extends to form a second extended strand, overcome the competition more efficiently.

(e) According to the PTOCE method developed by the present inventor, the PTO fragment generated by the cleavage of the PTO may comprises not only the 5'-tagging portion of the PTO but also some nucleotides at the 5'-end of the 3'-targeting portion of the PTO, depending upon the 5' nuclease used. Even if a plurality of PTOs having the same 5'-tagging portion are used to detect different target nucleic acid sequences, the nucleotide at the 3'-end of the PTO fragment thus generated may vary because the nucleotide at the 3'-end is dependent on the target nucleic acid sequence. Thus, in order to detect a variety of target nucleic acid sequences (e.g., screening approach), a plurality of labeled CTOs should be designed to be complementary to the nucleotide at the 3'-end of the PTO fragment. In contrast, the PTOCE-E method of the present invention can be performed in a cost-effective manner by using a plurality of types of first CTOs having no costly label and a single type of second CTOs having a label.

(f) The PTOCE-E method of the present invention can allow both the first extended strand and the second extended strand to provide signals in the detection of a single target nucleic acid sequence, thereby increasing the intensity of the target signal.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Detection of Target Nucleic Acid Sequence Using Probing and

Tagging Oligonucleotide Cleavage and Extension-Dependent Extension (PTOCE-E) Assay We examined whether the PTO cleavage and extension-dependent extension (PTOCE-E) assay according to the present invention can detect a target nucleic acid sequence in a real-time PCR manner.

<1-1> Preparation of Target Nucleic Acid Sequence and Oligonucleotides

Taq DNA polymerase having a 5' nuclease activity was used for the extension of forward primer and reverse primer, the cleavage of PTO, the extension of PTO fragment, and the further extension of first extended strand. In addition, a plasmid DNA containing wild-type KRAS (NCBI Accession No. NG_007524) gene was used as a target nucleic acid sequence.

The PTO was designed to have (i) a 3'-targeting portion comprising a hybridizing nucleotide sequence to the target nucleic acid sequence and (ii) a 5'-tagging portion comprising a non-hybridizing nucleotide sequence to the target nucleic acid sequence.

The first CTO to be hybridized with the PTO fragment was designed to have (i) a capturing portion comprising a hybridizing nucleotide sequence to the PTO fragment and (ii) a templating portion comprising a non-hybridizing nucleotide sequence to the both 5'-tagging portion and the 3'-targeting portion of the PTO.

In addition, the second CTO to be hybridized with the first extended strand was designed to have (i) a capturing portion comprising a hybridizing nucleotide sequence to the first extended strand (particularly, the first extended sequence) and (ii) a templating portion comprising a non-hybridizing nucleotide sequence to the first extended strand, the 5'-tagging portion and the 3'-targeting portion of the PTO. The second CTO was labeled with a quencher molecule (BHQ-1) at its 5'-end and with a fluorescent reporter molecule (CAL Fluor Red 610) at its templating portion.

The PTO, the first CTO, and the second CTO were blocked with a carbon spacer at their 3'-ends to prohibit their extension by a DNA polymerase.

The sequences of the forward primer, reverser primer, PTO, first CTO, and second CTO used in this Example are shown in Table 1 below.

denatured for 5 min at 50° C. and 15 min at 95° C. and subjected to 50 cycles of 10 sec at 95° C., 40 sec at 55° C. and 10 sec at 72° C. The detection of the signal was performed at 55° C. of each cycle. A threshold value of RFU 50 was applied to the amplification curve so as to determine the presence of the target nucleic acid sequence.

Figure 3:
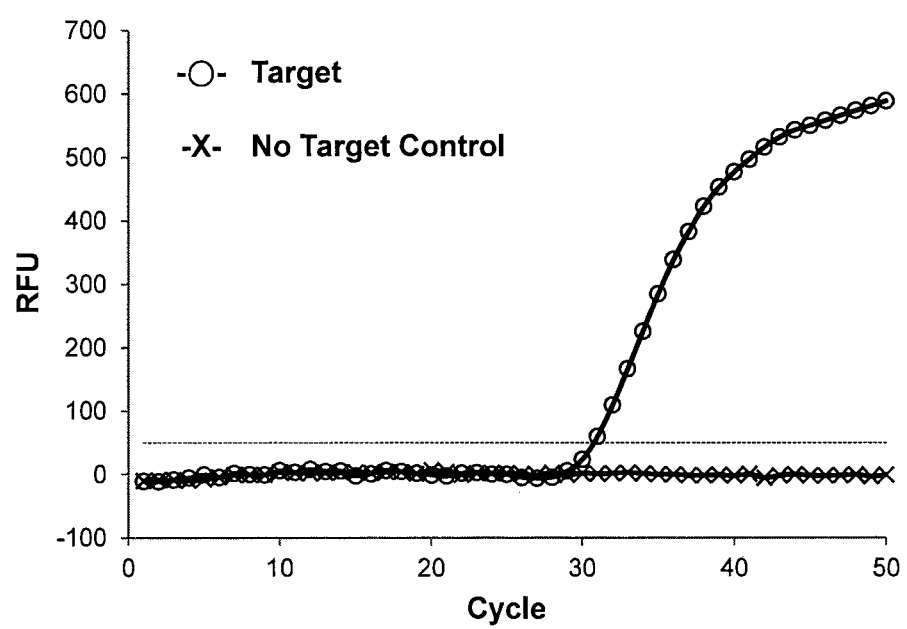
FIG. 3 shows the results of the detection of a target nucleic acid sequence (wild-type KRAS gene) by real-time PCR based on the PTOCE-E assay. In the figure, "-O-" represents the result for a sample containing the target nucleic acid sequence; "-X-" represents the result for a samples containing no target nucleic acid sequence (No Target Control).

As shown in in FIG. 3, a sample containing the target nucleic acid sequence (-O-) exhibited a target signal with a Ct value of 30.72, indicating the presence of the target nucleic acid sequence in the sample. In contrast, a sample containing no target nucleic acid sequence (-X-) did not exhibit a target signal above the threshold, indicating the absence of the target nucleic acid sequence in the sample.

The results demonstrate that the presence of the target nucleic acid sequence can be accurately determined using the PTOCE-E analysis of the present invention.

Example 2: Discrimination of Single Nucleotide Variation Using PTOCE-E Assay

We examined whether the PTOCE-E assay according to the present invention can distinguish target nucleic acid sequences having single nucleotide variation (SNV).

<1-1> Preparation of Target Nucleic Acid Sequence and Oligonucleotides

A plasmid DNA containing the wild-type KRAS gene (NCBI Accession No. NG_007524) and a plasmid DNA containing the mutant KRAS gene (NCBI Accession No. M_54968) were used as wild-type and mutant target nucleic acid sequences, respectively. The wild-type KRAS gene encodes glycine (GGT) at the $12^{th}$ amino acid position, while the mutant KRAS gene encodes cysteine (TGT) at the corresponding position (i.e., a single nucleotide variation from G to T).

Oligonucleotides for detecting the wild-type target nucleic acid sequence were prepared as in Example <1-1>.

TABLE 1

| Name | Type | Sequence (5' → 3') | SEQ ID NO |
|---|---|---|---|
| FPm | Forward Primer | ATGTTCTAATATAGTCACATTTTCATT | 1 |
| RPm | Reverse Primer | CTCTATTGTTGGATCATATTCGTC | 2 |
| PTO | PTO | <u>GTCGCGCGTAATC</u>GGTGGCGTAGGCAAGAGTGCCTTGA[C3 spacer] | 3 |
| CTO-1 | First CTO | GTACGCGGTCGACGGTGCGATTACGCGCGAC[C3 spacer] | 4 |
| CTO-2 | Second CTO | [BHQ-1]GGTGGATGACGCGCG[T(Cal Red 610)]TTTGTACGCGGTCGACGG[C3 spacer] | 5 |

<u>5'-tagging portion of PTO</u>
Bold letter: Mutation site

<1-2> Performing Real-Time PCR and Detecting Target Signal

The reaction was conducted in the final volume of 20 μl containing 5 pmole of forward primer (SEQ ID NO: 1), 5 pmole of reverse primer (SEQ ID NO: 3), 3 pmole of PTO (SEQ ID NO: 3), 0.5 pmole of first CTO (SEQ ID NO: 4), 1 pmole of second CTO (SEQ ID NO: 5), $10^5$ copies of wild-type target nucleic acid sequence, and 10 μl of 2× Master Mix (final, 200 μM of dNTPs, 2 mM MgCl$_2$, 2 units of Taq DNA polymerase (Enzynomics, Korea); the tube containing the reaction mixture was placed in the real-time thermocycler (CFX96, Bio-Rad); the reaction mixture was <2-2> Performing Real-Time PCR and Detecting Target Signal The reaction was conducted in the same manner as in the Example <1-2>, except for using 10 pmole of forward primer, 10 pmole of reverse primer, 3 pmole of PTO, 0.5 pmole of first CTO, 1 pmole of second CTO, $10^6$ copies of wild-type target nucleic acid sequence or mutant target nucleic acid sequence. Afterwards, a target signal was detected by real-time PCR.

Figure 4:
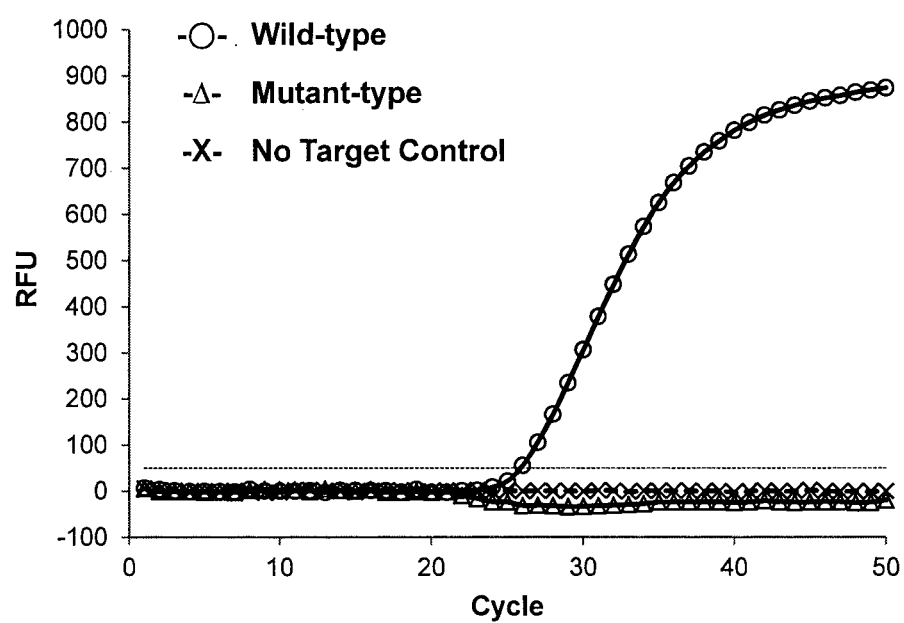
FIG. 4 shows the results of the detection of a nucleotide variation in a target nucleic acid sequence by real-time PCR based on the PTOCE-E assay. In the figure, "-O-" represents the result for a sample containing a target nucleic acid sequence having a wild-type KRAS gene; "-Δ-" represents the result for a sample containing a target nucleic acid sequence having a mutant KRAS gene; "-X-" represents the result for a sample containing no target nucleic acid sequence (No Target Control).

As shown in in FIG. 4, a sample containing the wild-type target nucleic acid sequence (-O-) exhibited a target signal with a Ct value of 25.84, indicating the presence of the wild-type target nucleic acid sequence in the sample. In contrast, a sample containing mutant target nucleic acid sequence (-Δ-), and a sample containing no wild-type and mutant target nucleic acid sequences (-X-) did not exhibit target signals above the threshold, indicating the absence of the wild-type target nucleic acid sequence in the sample.

The results above demonstrate that the single nucleotide variation in the target nucleic acid sequence can be distinguishably detected using the PTOCE-E analysis of the present invention. Even though this Example illustrates the detection of a wild-type target nucleic acid sequence, those skilled in the art will be able to detect a mutant target nucleic acid sequence in the same manner using oligonucleotides for detecting the mutant target nucleic acid sequence.

Having described a preferred embodiment of the present invention, it is to be understood that variants and modifications thereof falling within the spirit of the invention may become apparent to those skilled in this art, and the scope of this invention is to be determined by appended claims and their equivalents.

This application contains references to amino acid sequences and/or nucleic acid sequences which have been submitted herewith as the sequence listing text fie. The aforementioned sequence listing is hereby incorporated by reference in its entirety pursuant to 37 C.F.R. § 1.52(e).

What is claimed is:

1. A method for detecting a target nucleic acid sequence from a DNA or a mixture of nucleic acids by a PTOCE-E (PTO Cleavage and Extension-dependent Extension) assay, comprising:

(a) hybridizing the target nucleic acid sequence with an upstream oligonucleotide and a PTO (Probing and Tagging Oligonucleotide); wherein the upstream oligonucleotide comprises a hybridizing nucleotide sequence to the target nucleic acid sequence; wherein the PTO comprises (i) a 3'-targeting portion comprising a hybridizing nucleotide sequence to the target nucleic acid sequence and (ii) a 5'-tagging portion comprising a non-hybridizing nucleotide sequence to the target nucleic acid sequence; wherein the 3'-targeting portion of the PTO is hybridized with the target nucleic acid sequence and the 5'-tagging portion of the PTO is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity to release a PTO fragment comprising the 5'-tagging portion or a part of the 5'-tagging portion of the PTO;

(c) hybridizing the PTO fragment with a first CTO (Capturing and Templating Oligonucleotide); wherein the first CTO comprises in a 3' to 5' direction (i) a capturing portion comprising a hybridizing nucleotide sequence to the PTO fragment and (ii) a templating portion comprising a non-hybridizing nucleotide sequence to the PTO fragment; wherein the PTO fragment is hybridized with the capturing portion of the first CTO;

(d) performing an extension reaction using the resultant of the step (c) and a template-dependent nucleic acid polymerase; wherein the PTO fragment hybridized with the capturing portion of the first CTO is extended to generate a first extended strand comprising a first extended sequence complementary to the templating portion of the first CTO, thereby forming a first extended duplex between the first extended strand and the first CTO;

(e) hybridizing the first extended strand with a second CTO; wherein the second CTO comprises in a 3' to 5' direction (i) a capturing portion comprising a hybridizing nucleotide sequence to the first extended strand and (ii) a templating portion comprising a non-hybridizing nucleotide sequence to the first extended strand; wherein the first extended strand is hybridized with the capturing portion of the second CTO;

(f) performing an extension reaction using the resultant of the step (e) and a template-dependent nucleic acid polymerase; wherein the first extended strand hybridized with the capturing portion of the second CTO is further extended to generate a second extended strand comprising a second extended sequence complementary to the templating portion of the second CTO, thereby forming a second extended duplex between the second extended strand and the second CTO; and (g) detecting the presence of the second extended strand; whereby the presence of the second extended strand indicates the presence of the target nucleic acid sequence.

2. The method of claim 1, wherein the capturing portion of the second CTO comprises a hybridizing nucleotide sequence to the first extended sequence.

3. The method of claim 1, wherein the second extended duplex provides a detectable signal by (i) at least one label linked to the PTO fragment and/or the second CTO, (ii) a label incorporated into the first extended strand and/or the second extended strand during the extension reaction, (iii) a label incorporated into the first extended strand and/or the second extended strand during the extension reaction and at least one label linked to the second CTO, or (iv) an intercalating label; wherein the presence of the second extended strand is detected by measuring the signal from the second extended duplex.

4. The method of claim 1, wherein the second extended duplex comprises a label and a cleavage site for a nucleolytic enzyme, and the second extended duplex provides a detectable signal by the cleavage at the cleavage site; wherein the presence of the second extended strand in the step (g) is detected by cleaving the second extended duplex by the nucleolytic enzyme and measuring a signal generated by the cleavage.

5. The method of claim 1, wherein the method further uses a Signaling Oligonucleotide (SO); wherein the SO comprises a hybridizing nucleotide sequence to the second extended strand and a label; wherein the SO provides a detectable signal by hybridization with the second extended strand; wherein the presence of the second extended strand in the step (g) is detected by hybridizing the SO with the second extended strand and measuring the signal generated by the hybridization.

6. The method of claim 1, wherein the method further uses a Signaling Oligonucleotide (SO); wherein the SO comprises a hybridizing nucleotide sequence to the second extended strand and a label; wherein a hybrid between the SO and the second extended strand comprises a cleavage site for a nucleolytic enzyme; wherein the hybrid provides a detectable signal by the cleavage at the cleavage site; wherein the presence of the second extended strand in the step (g) is detected by cleaving the hybrid with the nucleolytic enzyme and measuring the signal generated by the cleavage.

7. The method of claim 1, wherein the method further uses a Hybridizing Oligonucleotide (HO); wherein the HO comprises a hybridizing nucleotide sequence to the second CTO and a label; wherein a hybrid between the HO and the second CTO provides a detectable signal; wherein the presence of the second extended strand in the step (g) is detected by measuring the signal from the hybrid; wherein the presence of the signal from the hybrid indicates the absence of the second extended strand.

8. The method of claim 1, wherein the method further uses an Immobilizing Oligonucleotide (IO) immobilized on a solid substrate; wherein the IO comprises a hybridizing nucleotide sequence to the second extended strand; wherein second extended strand comprises a label; wherein the IO provides a detectable signal by the hybridization with the second extended strand; wherein the presence of the second extended strand in the step (g) is detected by hybridizing the IO with the second extended strand and measuring the signal generated by the hybridization.

9. The method of claim 1, wherein the upstream oligonucleotide is an upstream primer or an upstream probe.

10. The method of claim 1, wherein the method further comprises repeating all or a portion of the steps (a)-(g) with denaturation.

11. The method of claim 1, wherein the enzyme having a 5' nuclease activity in the step (b), the template-dependent nucleic acid polymerase in the step (d), and the template-dependent nucleic acid polymerase in the step (f) are identical to one another.

12. The method of claim 1, wherein the target nucleic acid sequence comprises a nucleotide variation.

13. The method of claim 1, wherein the method is carried out in the presence of a label such that the first extended duplex additionally comprises at least one label, and further comprises detecting a target signal provided by the first extended duplex.

14. The method of claim 1, wherein the method is performed in the presence of a downstream primer.

15. A method for detecting a target nucleic acid sequence from a DNA or a mixture of nucleic acids by a PTOCE-E (PTO Cleavage and Extension-dependent Extension) assay, comprising:

(a) hybridizing the target nucleic acid sequence with an upstream oligonucleotide and a PTO (Probing and Tagging Oligonucleotide); wherein the upstream oligonucleotide comprises a hybridizing nucleotide sequence to the target nucleic acid sequence; wherein the PTO comprises (i) a 3'-targeting portion comprising a hybridizing nucleotide sequence to the target nucleic acid sequence and (ii) a 5'-tagging portion comprising a non-hybridizing nucleotide sequence to the target nucleic acid sequence; wherein the 3'-targeting portion of the PTO is hybridized with the target nucleic acid sequence and the 5'-tagging portion of the PTO is not hybridized with the target nucleic acid sequence; the upstream oligonucleotide is located upstream of the PTO;

(b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity to release a PTO fragment comprising the 5'-tagging portion or a part of the 5'-tagging portion of the PTO;

(c) hybridizing the PTO fragment with a first CTO (Capturing and Templating Oligonucleotide); wherein the first CTO comprises in a 3' to 5' direction (i) a capturing portion comprising a hybridizing nucleotide sequence to the PTO fragment and (ii) a templating portion comprising a non-hybridizing nucleotide sequence to the 5'-tagging portion and the 3'-targeting portion of the PTO; wherein the PTO fragment is hybridized with the capturing portion of the first CTO;

(d) performing an extension reaction using the resultant of the step (c) and a template-dependent nucleic acid polymerase; wherein the PTO fragment hybridized with the capturing portion of the first CTO is extended to generate a first extended strand comprising a first extended sequence complementary to the templating portion of the first CTO, thereby forming a first extended duplex between the first extended strand and the first CTO;

(e) hybridizing the first extended strand with a second CTO; wherein the second CTO comprises in a 3' to 5' direction (i) a capturing portion comprising a hybridizing nucleotide sequence to the first extended strand and (ii) a templating portion comprising a non-hybridizing nucleotide sequence to the first extended strand; wherein the first extended strand is hybridized with the capturing portion of the second CTO;

(f) performing an extension reaction using the resultant of the step (e) and a template-dependent nucleic acid polymerase; wherein the first extended strand hybridized with the capturing portion of the second CTO is further extended to generate a second extended strand comprising a second extended sequence complementary to the templating portion of the second CTO, thereby forming a second extended duplex between the second extended strand and the second CTO; and (g) detecting the presence of the first extended strand; whereby the presence of the first extended strand indicates the presence of the target nucleic acid sequence.

16. A kit for detecting a target nucleic acid sequence from a DNA or a mixture of nucleic acids by a PTOCE-E (PTO Cleavage and Extension-dependent Extension) assay, comprising:

(a) an upstream oligonucleotide comprising a hybridizing nucleotide sequence to the target nucleic acid sequence;

(b) a PTO (Probing and Tagging Oligonucleotide); wherein the PTO comprises (i) a 3'-targeting portion comprising a hybridizing nucleotide sequence to the target nucleic acid sequence and (ii) a 5'-tagging portion comprising a non-hybridizing nucleotide sequence to the target nucleic acid sequence; wherein the 3'-targeting portion of the PTO is hybridized with the target nucleic acid sequence and the 5'-tagging portion of the PTO is not hybridized with the target nucleic acid sequence; the upstream oligonucleotide is located upstream of the PTO; wherein the upstream oligonucleotide or its extended strand induces cleavage of the PTO by the enzyme having the 5' nuclease activity to release a PTO fragment comprising the 5'-tagging portion or a part of the 5'-tagging portion of the PTO;

(c) a first CTO (Capturing and Templating Oligonucleotide); wherein the first CTO comprises in a 3' to 5' direction (i) a capturing portion comprising a hybridizing nucleotide sequence to the PTO fragment and (ii) a templating portion comprising a non-hybridizing nucleotide sequence to the 5'-tagging portion and the 3'-targeting portion of the PTO; wherein the PTO fragment is hybridized with the capturing portion of the first CTO; the PTO fragment hybridized with the capturing portion of the first CTO is extended to generate a first extended strand comprising a first extended sequence complementary to the templating portion of the first CTO, thereby forming a first extended duplex between the first extended strand and the first CTO; and (d) a second CTO; wherein the second CTO comprises in a 3' to 5' direction (i) a capturing portion comprising a hybridizing nucleotide sequence to the first extended strand and (ii) a templating portion comprising a non-hybridizing nucleotide sequence to the first extended strand; wherein the first extended strand hybridized with the capturing portion of the second CTO is further extended to generate a second extended strand comprising a second extended sequence complementary to the templating portion of the second CTO, thereby forming a second extended duplex between the second extended strand and the second CTO.

17. The kit of claim 16, wherein the PTO, the first CTO, or the second CTO has a single label or an interactive dual label.

18. The kit of claim 16, wherein the kit further comprises (i) a label incorporated into the first extended duplex and/or the second extended duplex during the extension reaction, or (ii) an intercalating label.

19. The kit of claim 16, wherein the kit further comprises an enzyme having a 5' nuclease activity and a template-dependent nucleic acid polymerase or a template-dependent nucleic acid polymerase having a 5' nuclease activity.

20. A kit for detecting a target nucleic acid sequence from a DNA or a mixture of nucleic acids, comprising a second CTO (Capturing and Templating Oligonucleotide), comprising in a 3' to 5' direction:

(i) a capturing portion comprising a hybridizing nucleotide sequence to a first extended strand; and (ii) a templating portion comprising a non-hybridizing nucleotide sequence to the first extended strand;

wherein the first extended strand is formed by cleaving a PTO (Probing and Tagging Oligonucleotide) hybridized with the target nucleic acid sequence with the enzyme having the 5' nuclease activity to release a PTO fragment, hybridizing the PTO fragment with the capturing portion of a first CTO, and extending the PTO fragment by the template-dependent nucleic acid polymerase;

wherein the PTO comprises (i) a 3'-targeting portion comprising a hybridizing nucleotide sequence complementary to the target nucleic acid sequence, and (ii) a 5'-tagging portion comprising a nucleotide sequence non-complementary to the target nucleic acid sequence;

wherein the first CTO (Capturing and Templating Oligonucleotide) comprises in a 3' to 5' direction (i) a capturing portion comprising a hybridizing nucleotide sequence to the PTO fragment and (ii) a templating portion comprising a non-hybridizing nucleotide sequence to the 5'-tagging portion and the 3'-targeting portion of the PTO.

21. The kit of claim 20, wherein the kit further comprises the first CTO.

* * * * *